United States Patent
Shibuya et al.

(10) Patent No.: US 8,518,936 B2
(45) Date of Patent: Aug. 27, 2013

(54) METHOD FOR PREPARING ACID ADDITION SALTS OF POLYACIDIC BASIC COMPOUNDS

(75) Inventors: Kimiyuki Shibuya, Saitama (JP); Tadaaki Ohgiya, Saitama (JP); Takayuki Matsuda, Tokyo (JP)

(73) Assignee: Kowa Co., Ltd., Nagoya-shi (JP)

( * ) Notice: Subject to any disclaimer, the term of this patent is extended or adjusted under 35 U.S.C. 154(b) by 158 days.

(21) Appl. No.: 12/762,111

(22) Filed: Apr. 16, 2010

(65) Prior Publication Data

US 2010/0234599 A1 Sep. 16, 2010

Related U.S. Application Data

(62) Division of application No. 10/545,200, filed as application No. PCT/JP2004/002375 on Feb. 27, 2004, now Pat. No. 7,750,150.

(30) Foreign Application Priority Data

Feb. 28, 2003 (JP) ................................. 2003-052700

(51) Int. Cl.
  *A61K 31/55* (2006.01)
  *A61K 31/497* (2006.01)
  *C07D 243/08* (2006.01)
  *C07D 403/00* (2006.01)

(52) U.S. Cl.
  USPC .............. 514/218; 514/254.03; 514/254.08; 540/575; 544/370

(58) Field of Classification Search
  None
  See application file for complete search history.

(56) References Cited

U.S. PATENT DOCUMENTS

| 6,133,040 A | 10/2000 | Glattstein |
| 6,969,711 B2 | 11/2005 | Shibuya et al. |
| 6,998,486 B2 | 2/2006 | Shibuya et al. |
| 7,176,306 B2 | 2/2007 | Shibuya et al. |
| 7,223,764 B2 | 5/2007 | Shibuya et al. |

FOREIGN PATENT DOCUMENTS

| EP | 0987254 | 3/2000 |
| WO | WO 98/54153 | 12/1998 |
| WO | WO 00/32593 | 6/2000 |

OTHER PUBLICATIONS

Sigma-Aldrich, 1999, pp. 1444-1452.*
Berge. Journal of Pharmaceutical Sciences, 1977, 66(1), 1-19.*
Translated by Koji Nakanishi et al., "Borrison Boyd Yuki Kagaku (last part)", 6th edition, Tokyo Kagaku Dojin, pp. 1340-1366, 1994.
"pKa compilation", http://research.chem.psu.edu/brpgroup/pKa_compilation.pdf, accessed Mar. 21, 2008.
English Translation of "Organic Chemistry", Sixth Edition, Morrison Boyd, pp. 1057-1076 (pp. 1340-1366 in the Japanese version correspond to pp. 1057-1076 in the English version), 1992.
"pKa values or organic / inorganic acids", http://chemweb.unp.ac.za/chemistry/Physical_Data/pKa_values.htm, accessed Dec. 17, 2008.
references Serjeant et al., Ionization Constants of Organic Acids in Solution, 1979.
LaVoie et al., Chemical Reviews, 1996, 96(8), 3147-76.
Johnson et al., Journal of Physical Chemistry, 1965, 69, 74-86.
Lisa F Frey, et al., "Practical routes towards the synthesis of 2-halo- and 2-alkylamino-4 pyridinecarboxaldehydes", Tetrahedron Letters, vol. 42, Issue 39, Jul. 25, 2001, pp. 6815-6818 and two pages.

* cited by examiner

*Primary Examiner* — Noble Jarrell
(74) *Attorney, Agent, or Firm* — Oblon, Spivak, McClelland, Maier & Neustadt, L.L.P.

(57) ABSTRACT

Monohydrochloride acid addition salts of a polyacidic basic compound, or a water adduct having basic site(s) stronger than pyridine. These monohydrochlorides can be produced by reacting a polyacidic basic compound with an acid salt of pyridine.

30 Claims, 24 Drawing Sheets

METHOD FOR PREPARING ACID ADDITION SALTS OF POLYACIDIC BASIC COMPOUNDS

This application is a division of U.S. application Ser. No. 10/545,200, filed Aug. 11, 2005 (now U.S. Pat. No. 7,750, 150), which is a national-stage filing of PCT/JP04/02375, filed Feb. 27, 2004. Priority is also claimed to Japan 2003-052700, filed Feb. 28, 2003.

TECHNICAL FIELD

This invention relates to a method for preparing an acid addition salt of a polyacidic basic compound or a water adduct of the acid addition salt, which makes it possible to readily add a desired number of moles of an acid to the polyacidic basic compound.

BACKGROUND ART

Pharmaceutical compositions are well known to have significant differences in solubility, oral absorption, drug activity, stability and the like depending on the kind and crystallized type of their salts, even when they are made of the same ingredient in free form. For the development of a pharmaceutical composition, it is therefore extremely important to select an ingredient enabling itself to fulfill the most preferred conditions, based on the results obtained by making comprehensive analysis on the material's characteristics, such as chemical stability, bioavailability and physical stability (the degree of crystallinity and the degree of hydration), effects on pharmaceutical properties (hardness, disintegration property and elution property) and effects on pharmaceutical capabilities (formability, anticaking property and capacity).

Piperazine derivatives, which are categorized into polyacidic basic compounds and represented typically by 2-[4-[2-(benzimidazol-2-ylthio)ethyl]piperazin-1-yl]-N-[2,4-bis(methylthio)-6-methyl-3-pyridyl]acetamide, are useful as inhibitors against the enzyme (acyl coenzyme A cholesterol acyltransferase, ACAT) that catalyzes the synthesis of cholesterol into a cholesterol ester (WO 98/54153 Pamphlet).

Inhibition of ACAT is thought to prevent cholesterol absorption through the intestinal tract, and also to suppress the secretion of very-low-density lipoprotein into blood at the liver, leading to a reduction in blood cholesterol. Further, inhibition of ACAT suppresses the foaming of macrophages in artery walls, so atherosclerosis lesions are expected to shrink per se. ACAT inhibitors are, therefore, expected to be applicable for the treatment and prevention of various diseases such as hyperlipidemia, arteriosclerosis, cervical and cerebral arteriosclerosis, cerebrovascular accidents, ischemic heart diseases, coronary sclerosis, nephrosclerosis, arteriosclerotic nephrosclerosis, arteriolosclerotic nephrosclerosis, malignant nephrosclerosis, ischemic bowel diseases, acute mesenteric vaso-occlusion, chronic intestinal angina, ischemic colitis, aortic cancer, and arteriosclerosis obliterans (ASO), and numerous researches and developments are now under way.

Among the above-described piperazine derivatives useful as ACAT inhibitors, 2-[4-[2-(benzimidazol-2-ylthio)ethyl]piperazin-1-yl]-N-[2,4-bis(methylthio)-6-methyl-3-pyridyl]acetamide, for example, has a problem such that it crystallizes in the form of the free base, but its oral absorption is little well because its crystals are not uniform and its physical stability and water solubility are too low.

Solutions to the aforementioned problems have been attempted mainly by adding an acid to such polyacidic basic compounds to improve their oral absorption or the like and using them as acid addition salts. For example, 2-[4-[2-(benzimidazol-2-ylthio)ethyl]piperazin-1-yl]-N-[2,4-bis(methylthio)-6-methyl-3-pyridyl]acetamide can be substantially improved in water solubility and oral absorption by converting it into the tetrahydrochloride 2-water adduct with an excess amount of hydrochloric acid.

Nonetheless, it has been pointed out that the number of moles of the added acid affects the physical properties of the resulting acid addition salt of the polyacidic basic compound, and that the tetrahydrochloride 2-water adduct cannot avoid a low degree of crystallinity in its powder X-ray diffraction analysis; it is susceptible to dehydration and dehydrochlorination in a differential scanning thermal analysis; and it is also recognized as having high hygroscopicity in a hygroscopicity test. A further problem is also presumed in that tableting machines and aluminum sheets may undergo metal corrosion due to the residual of the acid used in excess and the strong acidity of the tetrahydrochloride. This raises concern about effects of the metal corrosion on the formulation of a pharmaceutical preparation and also on the stability of the pharmaceutical preparation. It is necessary to fully control factors such as drying temperature, vacuum (reduced pressured) level and drying degree upon preparation. Yet it is difficult to efficiently and stably supply such acid addition salts as active ingredients for pharmaceutical compositions while always providing them with uniform physical properties.

For the resolution of the above-described problems, it may be contemplated to prepare an acid addition salt with the number of moles of the acid to be added being controlled. However, there is still a problem in that when hydrochloric acid or the like is used as an acid, it is difficult to accurately measure the amount of the acid in a mole number desired to be added to 1 mole of a polyacidic basic compound, thereby becoming too hard to easily prepare the acid addition salt of the polyacidic basic compound, said salt containing the added acid in a desired number of moles, or a water adduct of the acid addition salt.

Accordingly, there has since been strong demand for a preparation method making it possible to easily adjust the number of moles of an acid in an acid addition salt of a polyacidic basic compound to a number suited for the polyacidic basic compound as needed.

DISCLOSURE OF THE INVENTION

An object of the present invention is to provide a preparation method which makes it possible to easily adjust the number of moles of an acid in an acid addition salt of a polyacidic basic compound, to a desired number.

With the foregoing circumstances in mind, the present inventors conducted an extensive investigation. As a result, it has been found that by reaction of a polyacidic basic compound with an acid salt of pyridine, said acid salt being formed from pyridine and an acid, it is readily possible to prepare an acid addition salt of the polyacidic basic compound with a desired number of moles of the acid being added to basic site(s) stronger than pyridine. It has also been found that acid addition salts of various piperazine derivatives, said acid addition salts being available from the practice of the above method, for example, 2-[4-[2-(benzimidazol-2-ylthio)ethyl]piperazin-1-yl]-N-[2,4-bis(methylthio)-6-methyl-3-pyridyl]acetamide monohydrochloride 0.9-water adduct has a high degree of crystallinity, has no hygroscopicity, is excellent in thermal stability without being accompanied with any substantial weight change by dehydration, dehydrochlorination and/or the like, does not develop the problem of polymorphism, and is free from the influence of any residual of hydrochloric acid, so that said compound is a preferred acid addition salt and is useful as a pharmaceutical ingredient. Based on these findings, the present invention has been completed.

Thus the present invention provides a method for the preparation of an acid addition salt of a polyacidic basic compound having basic site(s) stronger than pyridine or a water adduct of the acid addition salt, which comprises reacting the polyacidic basic compound with an acid salt of pyridine.

The present invention also provides 2-[4-[2-(benzimidazol-2-ylthio)ethyl]piperazin-1-yl]-N-[2,4-bis(methylthio)-6-methyl-3-pyridyl]acetamide monohydrochloride or a water adduct thereof, 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide monohydrochloride or a water adduct thereof, 2-[4-[2-(benzimidazol-2-ylthio)ethyl]piperazin-1-yl]-N-[2,4-bis(2,2,2-trifluoroethoxy)-6-methyl-3-pyridyl]acetamide dihydrochloride or a water adduct thereof, 2-[4-[2-(benzoxazol-2-ylthio)ethyl]piperazin-1-yl]-N-[2,4-bis(2,2,2-trifluoroethoxy)-6-methyl-3-pyridyl]acetamide monohydrochloride or a water adduct thereof, 2-[4-[2-(benzothiazol-2-ylthio)ethyl]piperazin-1-yl]-N-[2,6-dimethyl-4-trifluoromethyl-3-pyridyl]acetamide dihydrochloride or a water adduct thereof, 2-[4-[2-(5-trifluoromethylbenzoxazol-2-ylthio)ethyl]piperazin-1-yl]-N-[2,4-bis(methylthio)-6-methyl-3-pyridyl]acetamide monohydrochloride or a water adduct thereof, or 2-[4-[2-(benzoxazol-2-ylthio)ethyl]piperazin-1-yl]-N-[2-(2-methoxyethoxy)-4-(2,2,2-trifluoroethoxy)-6-methyl-3-pyridyl]acetamide monohydrochloride or a water adduct thereof.

The method of the present invention can easily prepare a salt of a polyacidic basic compound with a desired number of moles of an acid added thereto. According to this preparation method, it is possible not only to control the number of moles of an added acid, but also to firmly prepare an acid addition salt of a polyacidic basic compound which is unstable to the acid.

The use of the acid salt of pyridine relatively weakens the acidity of the acid, and substantially lessens the problems of the conventional method such as the decomposition, the formation of impurities and the like by a localized pH reduction in a system due to the addition or the like of a strong acid.

BEST MODES FOR CARRYING OUT THE INVENTION

Figure 1:
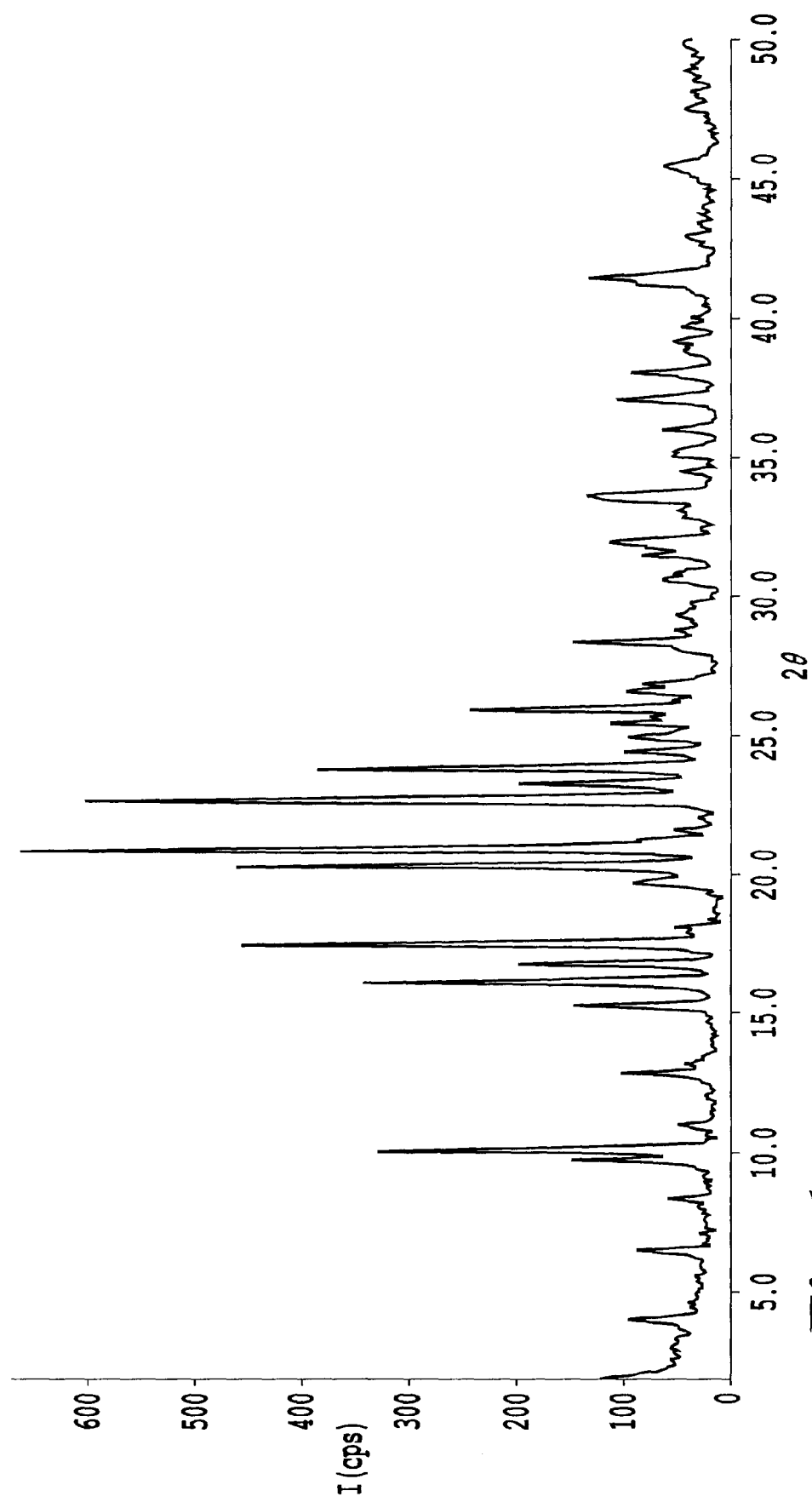
FIG. 1 shows a powder X-ray diffraction pattern of 2-[4-[2-(benzimidazol-2-ylthio)ethyl]piperazin-1-yl]-N-[2,4-bis(methylthio)-6-methyl-3-pyridyl]acetamide monohydrochloride 0.9-water adduct.

The polyacidic basic compound for use in the present invention is a compound having one or more basic sites stronger than pyridine, and its examples include nitrogen-containing compounds having plural ones of piperazino groups, tertiary amino groups, secondary amino groups, primary amino groups and the like in the same molecule. Preferred as the polyacidic basic compound are nitrogen-containing organic compounds, with piperazine derivatives being more preferred.

Preferred as the piperazine derivatives are those represented by the following formula (1):

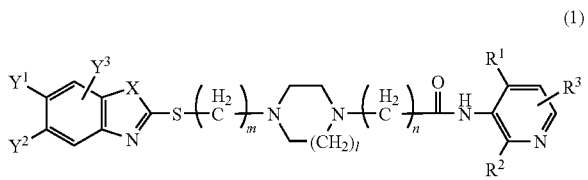

(1)

wherein X represents —NH—, an oxygen atom or a sulfur atom, $Y^1$, $Y^2$ and $Y^3$ each independently represent a hydrogen or halogen atom or a lower alkyl or lower haloalkyl group, $R^1$, $R^2$ and $R^3$ each independently represents a hydrogen or halogen atom or a lower alkyl, lower haloalkyl, lower alkylthio, lower haloalkoxy or lower alkoxyalkoxy group, l denotes an integer of from 1 to 2, m denotes an integer of from 2 to 4, and n denotes an integer of from 1 to 3. The term "lower" as used herein means a carbon number of from 1 to 5, with 1 to 3 being particularly preferred.

More preferred as the piperazine derivatives are those represented by the following formula (2):

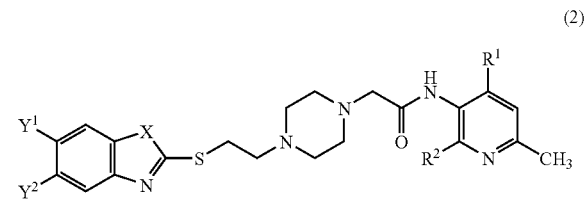

(2)

wherein X represents —NH—, an oxygen atom or a sulfur atom, $Y^1$ and $Y^2$ each independently represent a hydrogen or halogen atom or a trifluoromethyl group, $R^1$ and $R^2$ each independently represent a methyl, trifluoromethyl, methylthio, trifluoroethoxy or methoxyethoxy group. Particularly preferred are 2-[4-[2-(benzimidazol-2-ylthio)ethyl]piperazin-1-yl]-N-[2,4-bis(methylthio)-6-methyl-3-pyridyl]acetamide, 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide, 2-[4-[2-(benzimidazol-2-ylthio)ethyl]piperazin-1-yl]-N-[2,4-bis(2,2,2-trifluoroethoxy)-6-methyl-3-pyridyl]acetamide, 2-[4-[2-(benzoxazol-2-ylthio)ethyl]piperazin-1-yl]-N-[2,4-bis(2,2,2-trifluoroethoxy)-6-methyl-3-pyridyl]acetamide, 2-[4-[2-(benzothiazol-2-ylthio)ethyl]piperazin-1-yl]-N-[2,6-dimethyl-4-trifluoromethyl-3-pyridyl]acetamide, 2-[4-[2-(5-trifluoromethylbenzoxazol-2-ylthio)ethyl]piperazin-1-yl]-N-[2,4-bis(methylthio)-6-methyl-3-pyridyl]acetamide, and 2-[4-[2-(benzoxazol-2-ylthio)ethyl]piperazin-1-yl]-N-[2-(2-methoxyethoxy)-4-(2,2,2-trifluoroethoxy)-6-methyl-3-pyridyl]acetamide. These compounds can be prepared by the method disclosed WO 98/54153.

The acid salt of pyridine, which is for use in the present invention, is the salt of pyridine with an inorganic acid or organic acid, and no particular limitation is imposed on the acid which forms a salt with pyridine. Examples thereof include inorganic acids such as hydrochloric acid, sulfuric acid, nitric acid, phosphoric acid, sulfurous acid, nitrous acid, hydrobromic acid and hydroiodic acid; fatty acids such as acetic acid, butyric acid and stearic acid; polybasic acids such as oxalic acid, maleic acid, succinic acid and fumaric acid; hydroxycarboxylic acids such as citric acid, lactic acid, tartaric acid, malic acid, mandelic acid, salicylic acid, pamoic acid, pantothenic acid and gluconic acid; sulfonic acids such as ethanedisulfonic acid, benzenesulfonic acid, paratoluenesulfonic acid and methanesulfonic acid; acidic amino acids such as glutamic acid and aspartic acid; and trifluoroacetic acid, and tannic acid.

Preferred examples of the acid include hydrochloric acid, sulfuric acid, maleic acid, fumaric acid, tartaric acid, malic acid, citric acid, methanesulfonic acid and the like, with hydrochloric acid, sulfuric acid and maleic acid being more preferred, with hydrochloric acid being particularly preferred.

The acid salt of pyridine may be used no matter whether its form is in crystalline or non-crystalline.

In the preparation of said crystalline acid salt of pyridine, it is theoretically possible to obtain an acid salt of pyridine by reacting pyridine and an acid in equal equivalent amounts. Even so it is preferred that the reaction be performed by using pyridine in an excess amount relative to the acid in an anhydrous or water-containing organic solvent, for example, by using pyridine 1.0 to 1.5 times, more preferably 1.0 to 1.2 times as much as the acid in terms of equivalents. The acid salt of pyridine so formed can be purified by a conventional crystallization method making use of a solvent or the like.

When a crystalline acid salt of pyridine is reacted with the polyacidic basic compound in the present invention, the acid salt of pyridine is used generally in an amount sufficient to supply the acid in the same number of moles as the acid to be added to 1 mole of the polyacidic basic compound. Specifically, the amount of the acid salt of pyridine is subject to the kind and amount of a solvent to be used, and it is preferred that the acid salt of pyridine be used in an enough amount able to supply the acid 1.0 to 3.0 times, preferably 1.0 to 2.5 times as much as the number of moles of the acid to be added.

When the acid addition salt of the polyacidic basic compound is prepared by using a non-crystalline acid salt of pyridine, it is preferred that the reaction be performed in an anhydrous or water-containing organic solvent by adding to the polyacidic basic compound the acid 1.0 to 2.5 times, preferably 1.0 to 1.2 times as much as the amount corresponding to the number of moles of the acid to be added to 1 mole of the polyacidic basic compound and also pyridine 1.0 to 1.5 times in equivalents, preferably 1.0 to 1.2 times in equivalents as much as the amount of the acid to be used.

In a process for the preparation of the acid addition salt of the polyacidic basic compound, a salt interchange is observed to occur between the polyacidic basic compound and the acid salt of pyridine to form the acid addition salt of the polyacidic basic compound, when the polyacidic basic compound and the acid salt of pyridine in an amount necessary for the acid to be added are heated and dissolved in an organic solvent at 0 to 120° C., more preferably at room temperature to 100° C., especially preferably at the reflux temperature of the organic solvent used.

Examples of the organic solvent used in the above process include lower alcohols such as methanol, ethanol and isopropanol; ethers such as dioxane and tetrahydrofuran; and acetone and acetonitrile. Mixed solvents obtained by adding water to organic solvents are also usable.

No particular limitations are imposed on the kind and amount of the solvent to be used in the above process. It is nevertheless desirable to suitably choose the kind and amount of the solvent so that the yield of the acid addition salt of the polyacidic basic compound can be maximized.

The resulting acid addition salt of the polyacidic basic compound or the resulting water adduct of the acid addition salt can be obtained by collecting precipitated crystals optionally after allowing the reaction mixture to stand for 0.5 to 24 hours under stirring and the reaction product to crystallize out.

The acid salt of pyridine of the present invention has an activity to weaken the acidity of the acid employed, so when the free form of the polyacidic basic compound becomes unstable to the acid, it can significantly alleviate problems such as the decomposition of the active ingredient and the formation of impurities due to a localized pH reduction in the system by the addition or the like of the strong acid in the conventional methods.

The preparation method of the present invention is extremely advantageous for the preparation of acid addition salts of the above-described piperazine derivatives, especially 2-[4-[2-(benzimidazol-2-ylthio)ethyl]piperazin-1-yl]-N-[2,4-bis(methylthio)-6-methyl-3-pyridyl]acetamide monohydrochloride or a water adduct thereof, 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide monohydrochloride or a water adduct thereof, 2-[4-[2-(benzimidazol-2-ylthio)ethyl]piperazin-1-yl]-N-[2,4-bis(2,2,2-trifluoroethoxy)-6-methyl-3-pyridyl]acetamide dihydrochloride or a water adduct thereof, 2-[4-[2-(benzoxazol-2-ylthio)ethyl]piperazin-1-yl]-N-[2,4-bis(2,2,2-trifluoroethoxy)-6-methyl-3-pyridyl]acetamide monohydrochloride or a water adduct thereof, 2-[4-[2-(benzothiazol-2-ylthio)ethyl]piperazin-1-yl]-N-[2,6-dimethyl-4-trifluoromethyl-3-pyridyl]acetamide dihydrochloride or a water adduct thereof, 2-[4-[2-(5-trifluoromethylbenzoxazol-2-ylthio)ethyl]piperazin-1-yl]-N-[2,4-bis(methylthio)-6-methyl-3-pyridyl]acetamide monohydrochloride or a water adduct thereof, and 2-[4-[2-(benzoxazol-2-ylthio)ethyl]piperazin-1-yl]-N-[2-(2-methoxyethoxy)-4-(2,2,2-trifluoroethoxy)-6-methyl-3-pyridyl]acetamide monohydrochloride or a water adduct thereof. Namely, no problem is existing with preparing 2-[4-[2-(benzimidazol-2-ylthio)ethyl]piperazin-1-yl]-N-[2,4-bis(methylthio)-6-methyl-3-pyridyl]acetamide tetrahydrochloride 2-water adduct, given the use of hydrochloric acid in an excess amount. However, even if there is a need that an amount of hydrochloric be precisely weighed as in the case of the preparation of a monohydrochloride or a water adduct thereof, it would be extremely difficult not only to conduct its operation, but also to obtain the desired uniform hydrochloride or its water adduct.

When preparing 2-[4-[2-(benzimidazol-2-ylthio)ethyl]piperazin-1-yl]-N-[2,4-bis(methylthio)-6-methyl-3-pyridyl]acetamide monohydrochloride or a water adduct thereof, 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide monohydrochloride or a water adduct thereof, 2-[4-[2-(benzimidazol-2-ylthio)ethyl]piperazin-1-yl]-N-[2,4-bis(2,2,2-trifluoroethoxy)-6-methyl-3-pyridyl]acetamide dihydrochloride or a water adduct thereof, 2-[4-[2-(benzoxazol-2-ylthio)ethyl]piperazin-1-yl]-N-[2,4-bis(2,2,2-trifluoroethoxy)-6-methyl-3-pyridyl]acetamide monohydrochloride or a water adduct thereof, 2-[4-[2-(benzothiazol-2-ylthio)ethyl]piperazin-1-yl]-N-[2,6-dimethyl-4-trifluoromethyl-3-pyridyl]acetamide dihydrochloride or a water adduct thereof, 2-[4-[2-(5-trifluoromethylbenzoxazol-2-ylthio)ethyl]piperazin-1-yl]-N-[2,4-bis(methylthio)-6-methyl-3-pyridyl]acetamide monohydrochloride or a water adduct thereof, and 2-[4-[2-(benzoxazol-2-ylthio)ethyl]piperazin-1-yl]-N-[2-(2-methoxyethoxy)-4-(2,2,2-trifluoroethoxy)-6-methyl-3-pyridyl]acetamide monohydrochloride or a water adduct thereof, use of a water-containing lower alcohol as an organic solvent is preferred.

In particular, 2-[4-[2-(benzimidazol-2-ylthio)ethyl]piperazin-1-yl]-N-[2,4-bis(methylthio)-6-methyl-3-pyridyl]acetamide monohydrochloride 0.9-water adduct obtained as described above has a high degree of crystallinity, does not have hygroscopicity, is excellent in thermal stability without any a weight change due to dehydration, dehydrochlorination or the like, has no problem of polymorphism, and is free from influence by a residual of hydrochloric acid, so this is a preferred acid addition salt.

EXAMPLES

The present invention will hereinafter be described in further detail on the basis of Examples, although the present invention should not be construed as being confined to the following Examples.

Example 1

Preparation of 2-[4-[2-(benzimidazol-2-ylthio)ethyl] piperazin-1-yl]-N-[2,4-bis(methylthio)-6-methyl-3-pyridyl]acetamide monohydrochloride 0.9-Water Adduct (1) After heating and dissolving the free base (2.00 kg, 3.98 mol) of 2-[4-[2-(benzimidazol-2-ylthio)ethyl]piperazin-1-yl]-N-[2,4-bis(methylthio)-6-methyl-3-pyridyl]acetamide and pyridine hydrochloride (0.92 kg, 7.96 mol) in ethanol (12 L) at reflux temperature, water (20 L) was added dropwise to the reaction mixture at 75 to 87° C. The reaction mixture was allowed to cool down to room temperature, and was stirred for 1 hour. Precipitated crystals were collected by filtration. The crystals were washed with water and dried at 80° C. under reduced pressure to obtain 2-[4-[2-(benzimidazol-2-ylthio)ethyl]piperazin-1-yl]-N-[2,4-bis(methylthio)-6-methyl-3-pyridyl]acetamide monohydrochloride water adduct (1.96 kg, 89.0%; found to contain 2% of ethanol from $^1$H-NMR) as colorless needles.

(2) 2-[4-[2-(Benzimidazol-2-ylthio)ethyl]piperazin-1-yl]-N-[2,4-bis(methylthio)-6-methyl-3-pyridyl]acetamide monohydrochloride water adduct (1.96 kg) prepared in the procedure (1) was suspended in water (40 L), and at reflux temperature, the solvent (20 L) was distilled off under the environmental pressure. After allowing the residue to cool down to room temperature, precipitated crystals were collected by filtration, washed with water and dried at 80° C. under reduced pressure to obtain the title compound (1.70 kg, 84.2%) as colorless needles.

Melting point: 194-196° C.
IR(KBr)cm$^{-1}$: 3431, 1674, 1625, 1564, 1520.
$^1$H-NMR (400 MHz, DMSO-d$_6$) δ: 2.32 (3H, s), 2.40 (3H, s), 2.45 (3H, s), 2.75-3.75 (14H, m), 6.92 (1H, m), 7.08-7.20 (2H, m), 7.42-7.53 (2H, m), 9.38 (1H, br s).

Elemental analysis for $C_{23}H_{30}N_6OS_2 \cdot HCl \cdot 0.9H_2O$ (in view of 2.84% water content as determined by a water content test):
Calculated: C, 49.74; H, 5.95; N, 15.13; Cl, 6.38; S, 17.32
Found: C, 49.97; H, 6.00; N, 15.24; Cl, 6.48; S, 17.26

Referential Example 1

Preparation of 2-[4-[2-(benzimidazol-2-ylthio)ethyl] piperazin-1-yl]-N-[2,4-bis(methylthio)-6-methyl-3-pyridyl]acetamide tetrahydrochloride 2-Water Adduct The free base (134.31 g, 0.267 mol) of 2-[4-[2-(benzimidazol-2-ylthio)ethyl]piperazin-1-yl]-N-[2,4-bis(methylthio)-6-methyl-3-pyridyl]acetamide was dissolved in methanol (500 mL), followed by the dropwise addition of 10% (w/v) hydrogen chloride in methanol (607.6 g, 1.666 mol) over 15 minutes under stirring at 0° C. Diethyl ether (700 mL) was added, and the mixture was left over for 2 hours. Precipitated crystals were collected by filtration, washed successively with a 1:1 mixed solvent (500 mL) of methanol-diethyl ether and diethyl ether (500 mL), and dried at room temperature for 3 hours under reduced pressure to afford the title compound (133.54 g, 73.0%) as colorless crystals.

Melting point: 193-196° C.
IR(KBr)cm$^{-1}$: 3405, 2922, 1699, 1614, 1564, 1516.
$^1$H-NMR (400 MHz, DMSO-d$_6$) δ: 2.42 (3H, s), 2.43 (3H, s), 2.46 (3H, s), 3.66-3.84 (10H, m), 3.91 (2H, t, J=7.3 Hz), 4.09 (2H, br s), 6.95 (1H, s), 7.33-7.43 (2H, m), 7.63-7.69 (2H, m), 10.16 (1H, br s).
Elemental analysis for C$_{23}$H$_{30}$N$_6$OS$_2$.4HCl.2H$_2$O:
Calculated: C, 40.35; H, 5.59; N, 12.28; Cl, 20.71; S, 14.05
Found: C, 40.12; H, 5.83; N, 12.13; Cl, 20.59; S, 14.27

Referential Example 2

Preparation of 2-[4-[2-(benzimidazol-2-ylthio)ethyl]piperazin-1-yl]-N-[2,4-bis(methylthio)-6-methyl-3-pyridyl]acetamide disulfate 1.5-Water Adduct Sulfuric acid (purity: 96%, 799.9 mg, 7.83 mmol) was diluted with water (1.5 mL). The free base (1.94 g, 3.86 mmol) of 2-[4-[2-(benzimidazol-2-ylthio)ethyl]piperazin-1-yl]-N-[2,4-bis(methylthio)-6-methyl-3-pyridyl]acetamide was added to the above diluted sulfuric acid, and dissolved at room temperature.

Ethanol (4.5 mL) was added, and a viscous substance formed was dissolved under heat. The solution was stirred at room temperature for 10 minutes, followed by the further addition of ethanol (9 mL). The mixture was chilled under stirring in ice water. Precipitated crystals were collected by filtration, and heated and dried at 80° C. for 3 hours under reduced pressure to afford the title compound (2.64 g, 94.3%) as a colorless powder.

Melting point: 204-208° C.
IR(KBr)cm$^{-1}$: 3403, 1700, 1617, 1567, 1521.
$^1$H-NMR (400 MHz, DMSO-d$_6$, 120° C.) δ: 2.44 (3H, s), 2.46 (3H, s), 2.48 (3H, s), 3.05-3.14 (4H, m), 3.26-3.53 (8H, m), 3.60 (2H, m), 6.92 (1H, m), 7.16-7.19 (2H, m), 7.48-7.52 (2H, m), 9.18 (1H, br s).
Elemental analysis for C$_{23}$H$_{30}$N$_6$OS$_3$.2H$_2$SO$_4$.1.5H$_2$O:
Calculated: C, 38.06; H, 5.14; N, 11.58; S, 22.09
Found: C, 37.99; H, 5.20; N, 11.39; S, 22.27

Referential Example 3

Preparation of 2-[4-[2-(benzimidazol-2-ylthio)ethyl]piperazin-1-yl]-N-[2,4-bis(methylthio)-6-methyl-3-pyridyl]acetamide monosulfate 4-Water Adduct The free base (2.95 g, 5.86 mmol) of 2-[4-[2-(benzimidazol-2-ylthio)ethyl]piperazin-1-yl]-N-[2,4-bis(methylthio)-6-methyl-3-pyridyl]acetamide was heated and dissolved at 80° C. for 2 minutes in 1 mol/L sulfuric acid (6 mL, 6.00 mmol). The solution was left over at room temperature for 3 days to induce precipitation of crystals. Subsequent to decantation, water (15 mL) was added, crystals were collected by filtration, successively washed with water (15 mL) and isopropanol (10 mL+5 mL), and left over (dried in the air) at room temperature under environmental pressure for 24 hours in an open system to afford the title compound (3.71 g, 94.1%) as colorless prisms.

Melting point: Unspecified.
IR(KBr)cm$^{-1}$: 3431, 1674, 1625, 1564, 1520.
$^1$H-NMR (400 MHz, DMSO-d$_6$) δ: 2.40 (6H, s), 2.45 (3H, s), 2.80-3.72 (14H, m), 6.92 (1H, m), 7.11-7.18 (2H, m), 7.43-7.53 (2H, m), 9.38 (1H, br s).
Elemental analysis for C$_{23}$H$_{30}$N$_6$OS$_3$.H$_2$SO$_4$.4H$_2$O:
Calculated: C, 41.06; H, 5.99; N, 12.49; S, 19.06
Found: C, 40.92; H, 5.85; N, 12.35; S, 19.07

Referential Example 4

Preparation of 2-[4-[2-(benzimidazol-2-ylthio)ethyl]piperazin-1-yl]-N-[2,4-bis(methylthio)-6-methyl-3-pyridyl]acetamide monosulfate The 2-[4-[2-(benzimidazol-2-ylthio)ethyl]piperazin-1-yl]-N-[2,4-bis(methylthio)-6-methyl-3-pyridyl]acetamide monosulfate 4-water adduct (3.25 g, 4.83 mmol), which had been prepared in Referential Example 3, was heated under reflux and dissolved in 97.5% ethanol (120 mL). The solution was left over at room temperature for 3 days to induce precipitation of crystals. The crystals were collected by filtration, washed with ethanol (30 mL+20 mL), and heated and dried at 80° C. for 6 hours under reduced pressure to afford the title compound (2.70 g, 93.0%) as colorless fine needles.

Melting point: 170-171° C.
IR(KBr)cm$^{-1}$: 3431, 1674, 1625, 1564, 1520.
$^1$H-NMR (400 MHz, DMSO-d$_5$) δ: 2.40 (6H, s), 2.45 (3H, s), 2.80-3.72 (14H, m), 6.92 (1H, m), 7.11-7.18 (2H, m), 7.43-7.53 (2H, m), 9.38 (1H, br s).
Elemental analysis for C$_{23}$H$_{30}$N$_6$OS$_3$.H$_2$SO$_4$:
Calculated: C, 45.98; H, 5.37; N, 13.99; S, 21.35
Found: C, 45.73; H, 5.40; N, 13.75; S, 21.38

Referential Example 5

Preparation of 2-[4-[2-(benzimidazol-2-ylthio)ethyl]piperazin-1-yl]-N-[2,4-bis(methylthio)-6-methyl-3-pyridyl]acetamide dimaleate The free base (23.75 g, 47.2 mmol) of 2-[4-[2-(benzimidazol-2-ylthio)ethyl]piperazin-1-yl]-N-[2,4-bis(methylthio)-6-methyl-3-pyridyl]acetamide was dissolved in ethanol (200 mL). Maleic acid (11.4 g, 98.2 mol) was added and dissolved under heat to prepare a homogeneous solution. The reaction mixture was concentrated under reduced pressure and the residue was crystallized from ethanol-ethyl acetate. The crystals were collected by filtration to afford the title compound (30.95 g, 89.1%) as colorless crystals.

Melting point: 127-130° C.
IR(KBr)cm$^{-1}$: 3424, 1687, 1624, 1576, 1492.
$^1$H-NMR (400 MHz, DMSO-d$_5$) δ: 2.43 (3H, s), 2.45 (3H, s), 2.47 (3H, s), 2.93-3.00 (4H, m), 3.08-3.17 (4H, m), 3.25 (2H, t, J=6.8 Hz), 3.37 (2H, br s), 3.55 (2H, t, J=6.8 Hz), 6.14 (4H, s), 6.91 (1H, s), 7.13-7.16 (2H, m), 7.44-7.50 (2H, m), 9.04 (1H, br s).
Elemental analysis for C$_{23}$H$_{30}$N$_6$OS$_3$.2C$_4$H$_4$O$_4$ (maleic acid):
Calculated: C, 50.67; H, 5.21; N, 11.44; S, 13.09
Found: C, 50.49; H, 5.37; N, 11.20; S, 13.36

Figure 2:
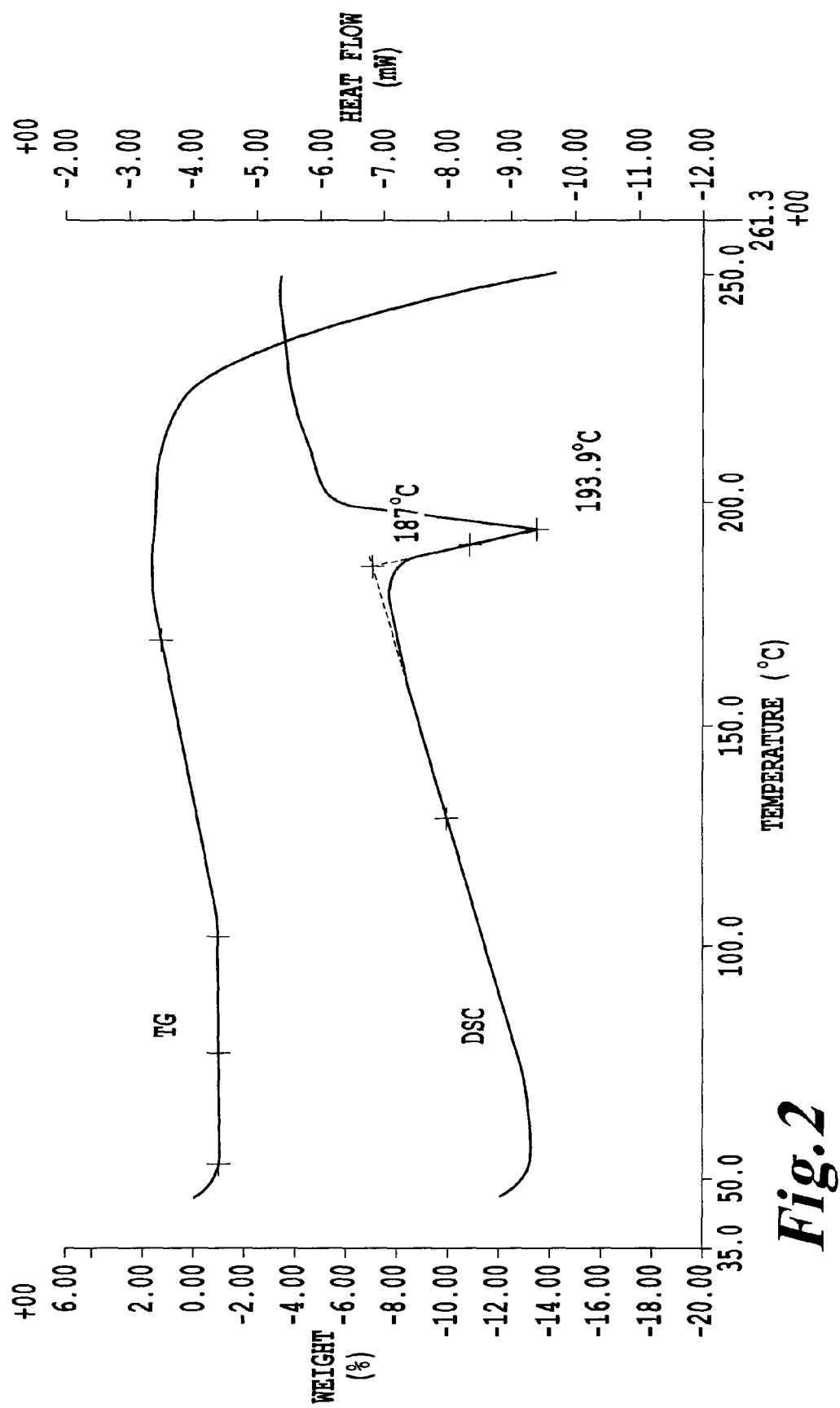
FIG. 2 shows the results of TG-DSC measurements of 2-[4-[2-(benzimidazol-2-ylthio)ethyl]piperazin-1-yl]-N-[2,4-bis(methylthio)-6-methyl-3-pyridyl]acetamide monohydrochloride 0.9-water adduct.
Figure 3:
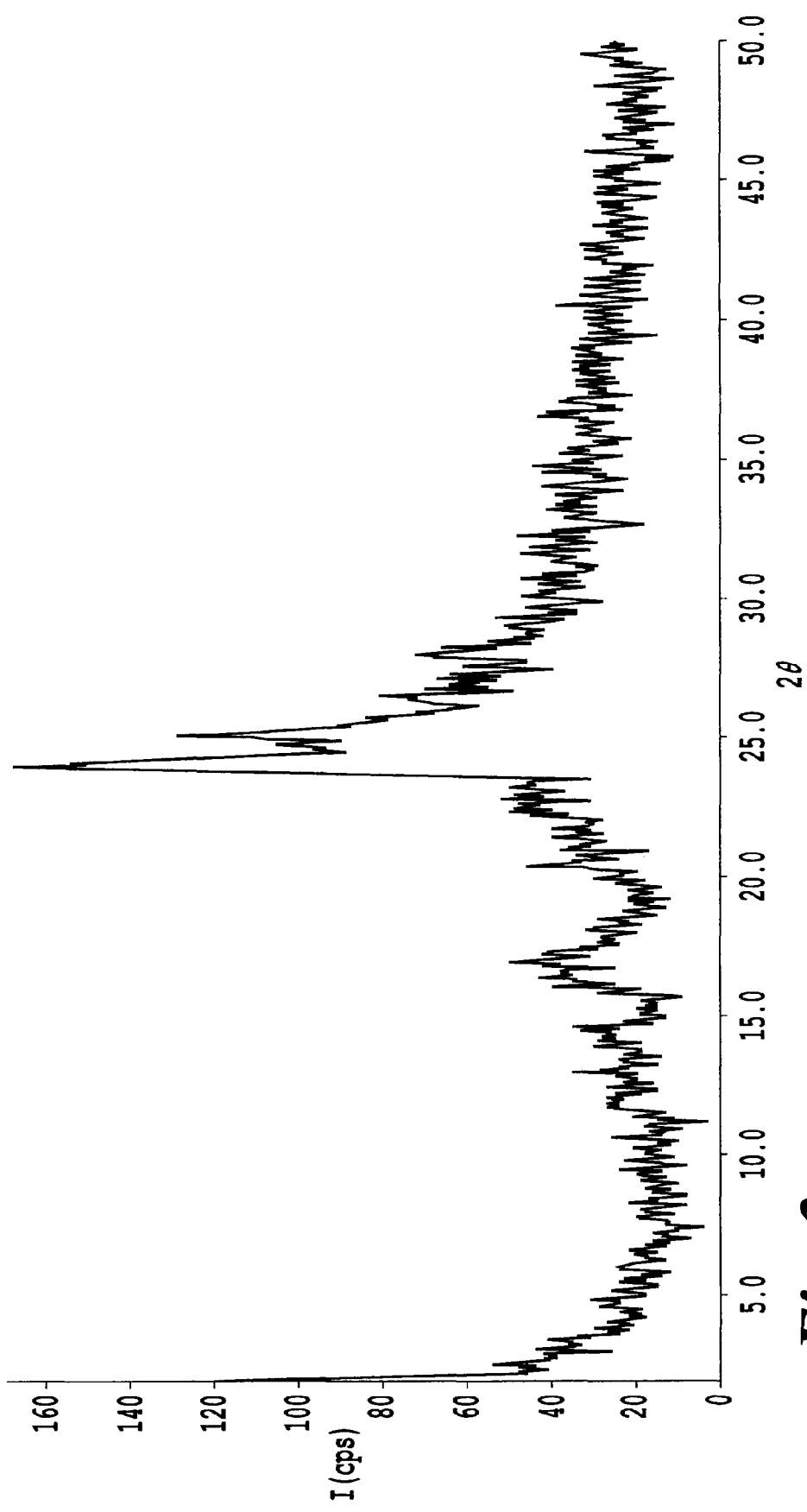
FIG. 3 shows a powder X-ray diffraction pattern of 2-[4-[2-(benzimidazol-2-ylthio)ethyl]piperazin-1-yl]-N-[2,4-bis(methylthio)-6-methyl-3-pyridyl]acetamide tetrahydrochloride 2-water adduct.
Figure 4:
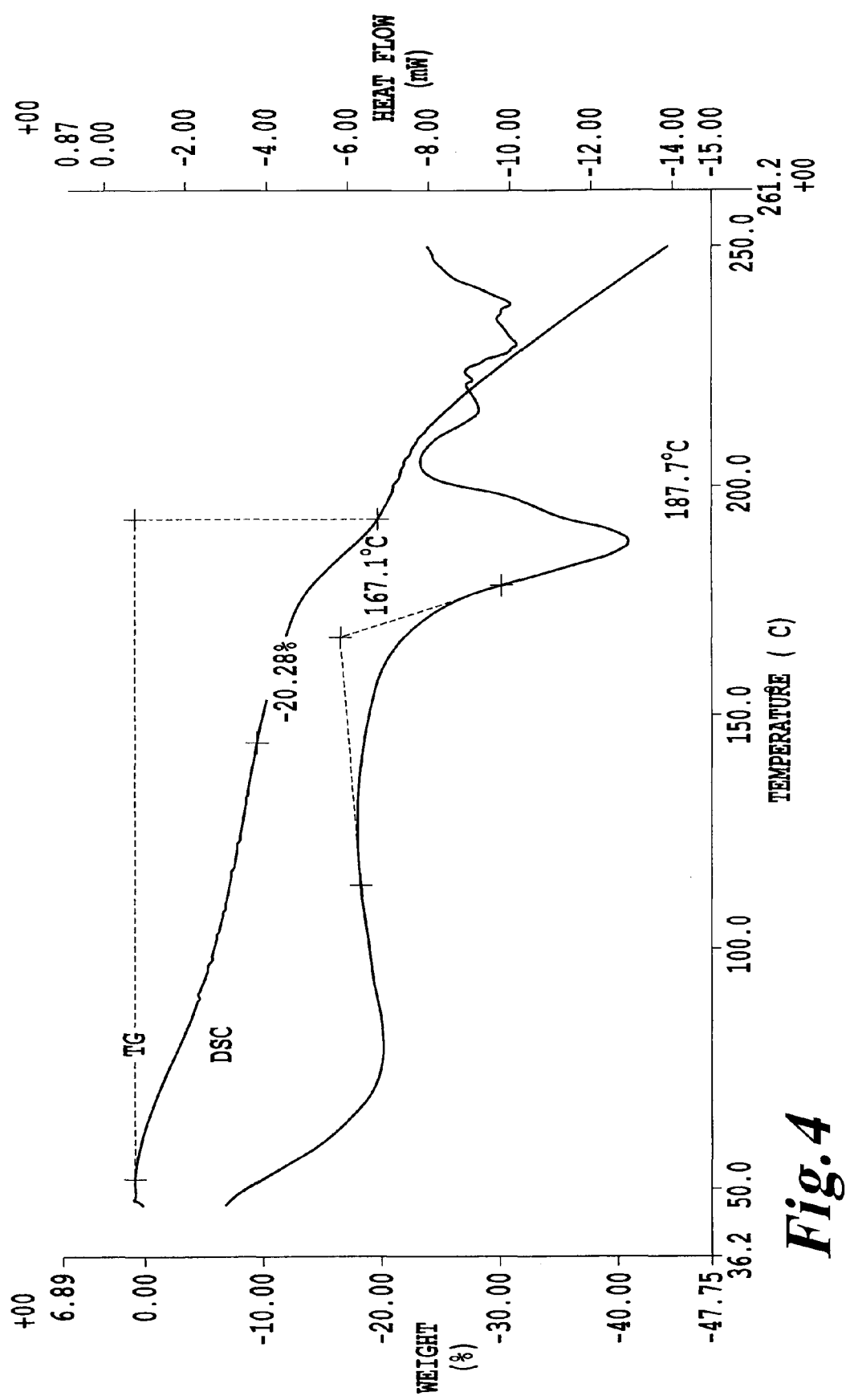
FIG. 4 shows the results of TG-DSC measurements of 2-[4-[2-(benzimidazol-2-ylthio)ethyl]piperazin-1-yl]-N-[2,4-bis(methylthio)-6-methyl-3-pyridyl]acetamide tetrahydrochloride 2-water adduct.
Figure 5:
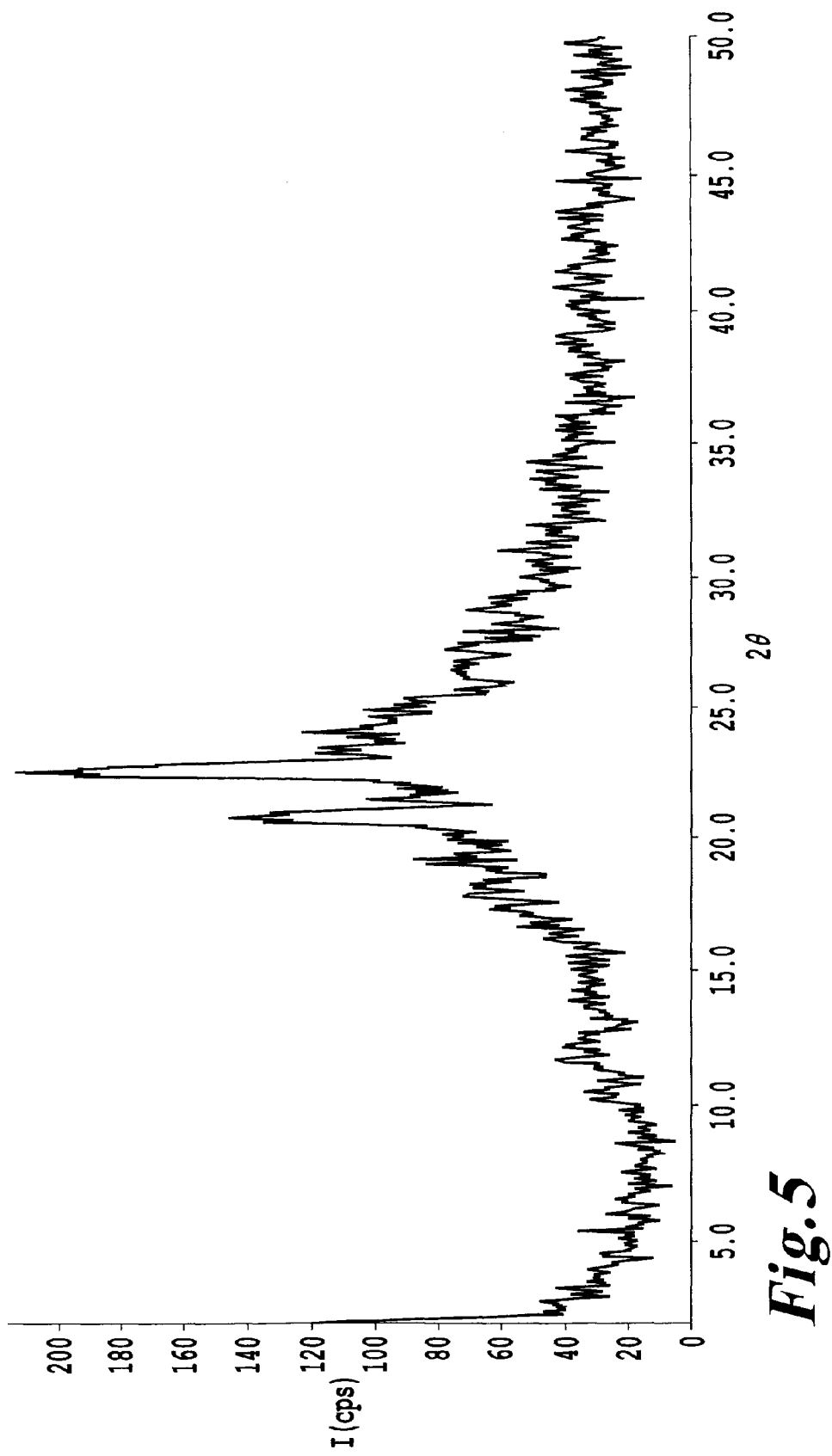
FIG. 5 shows a powder X-ray diffraction pattern of 2-[4-[2-(benzimidazol-2-ylthio)ethyl]piperazin-1-yl]-N-[2,4-bis(methylthio)-6-methyl-3-pyridyl]acetamide disulfate 1.5-water adduct.
Figure 6:
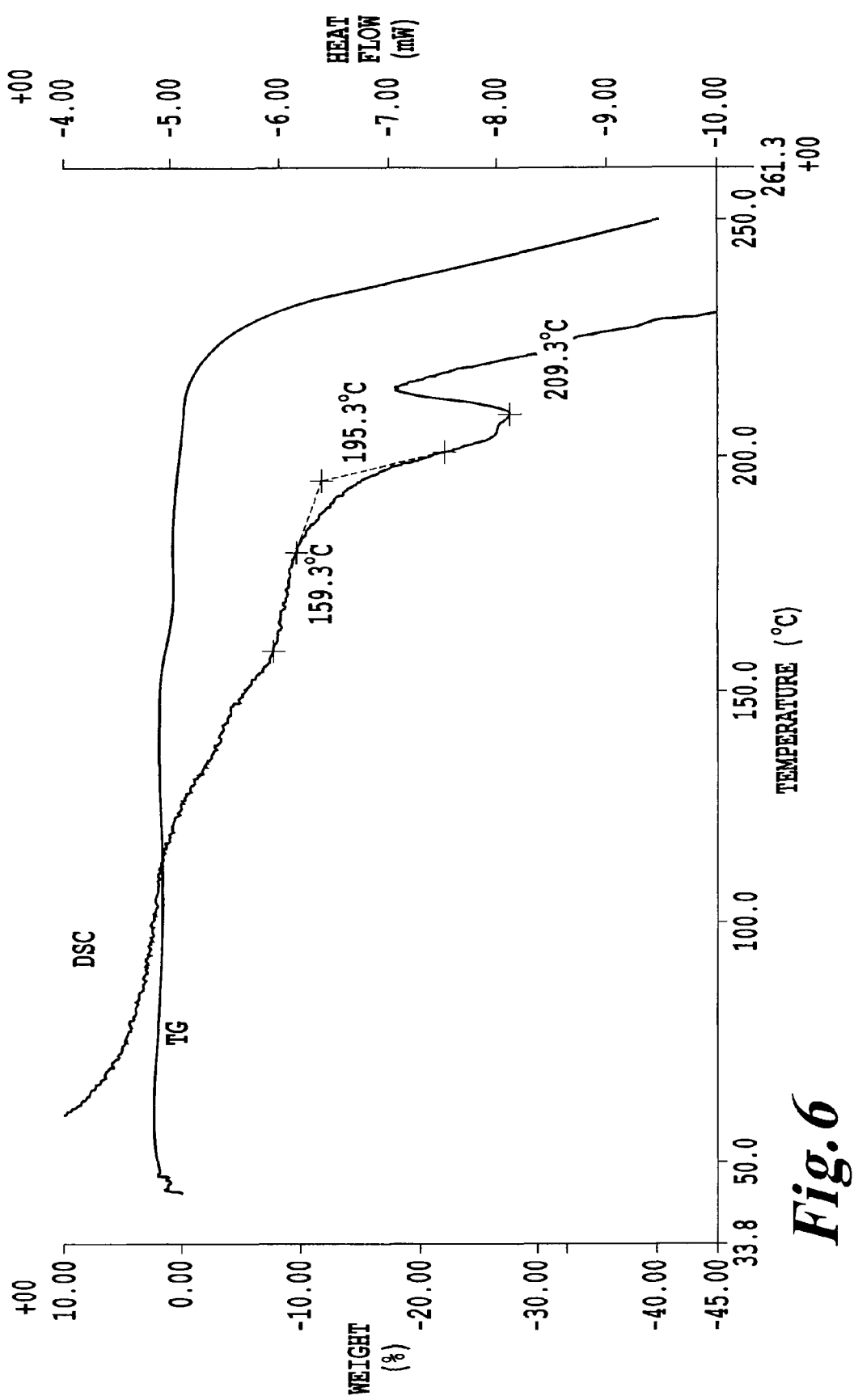
FIG. 6 shows the results of TG-DSC measurements of 2-[(4-[2-(benzimidazol-2-ylthio)ethyl]piperazin-1-yl]-N-[2,4-bis(methylthio)-6-methyl-3-pyridyl]acetamide disulfate 1.5-water adduct.
Figure 7:
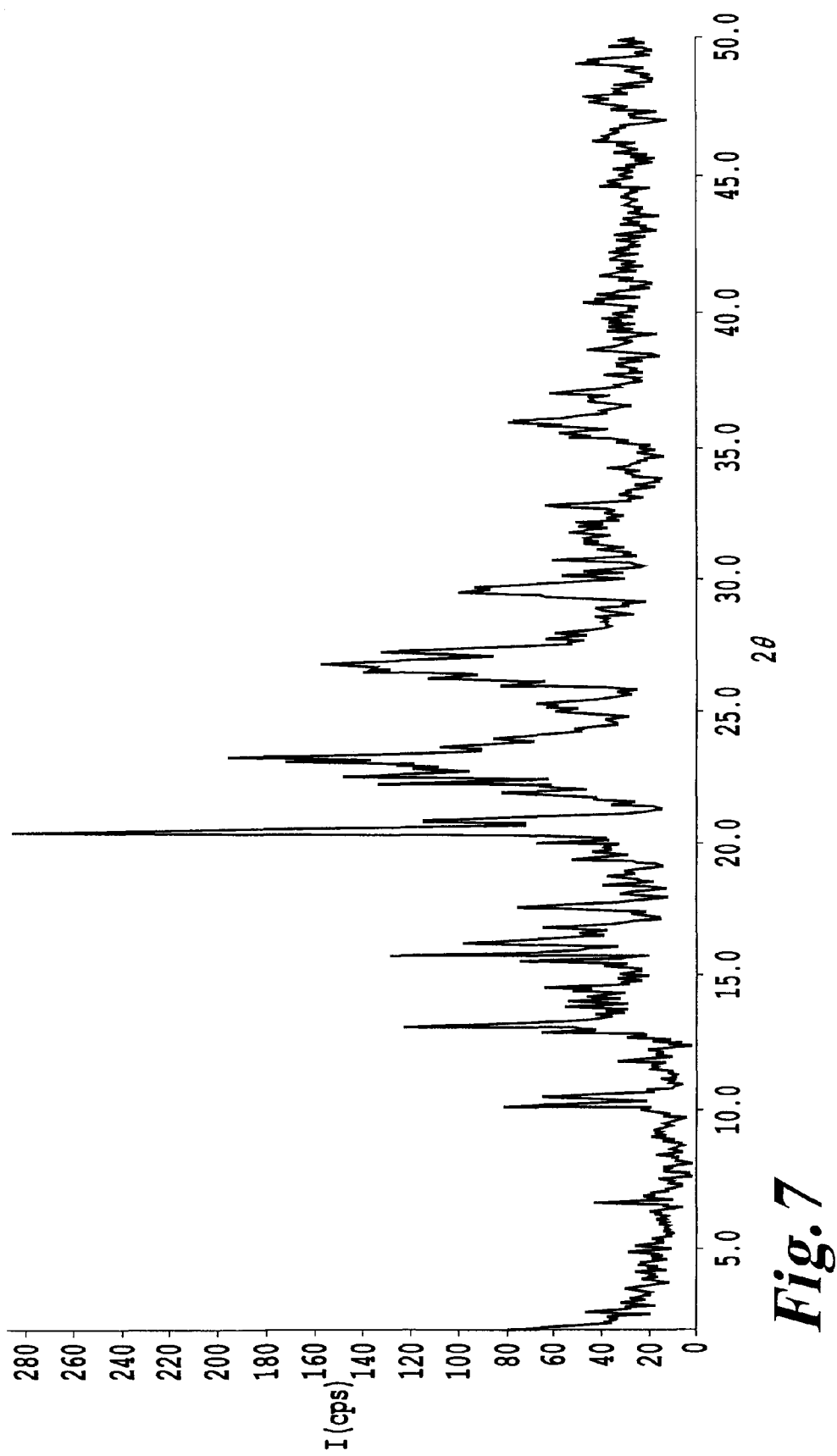
FIG. 7 shows a powder X-ray diffraction pattern of 2-[4-[2-(benzimidazol-2-ylthio)ethyl]piperazin-1-yl]-N-[2,4-bis(methylthio)-6-methyl-3-pyridyl]acetamide monosulfate 4-water adduct.
Figure 8:
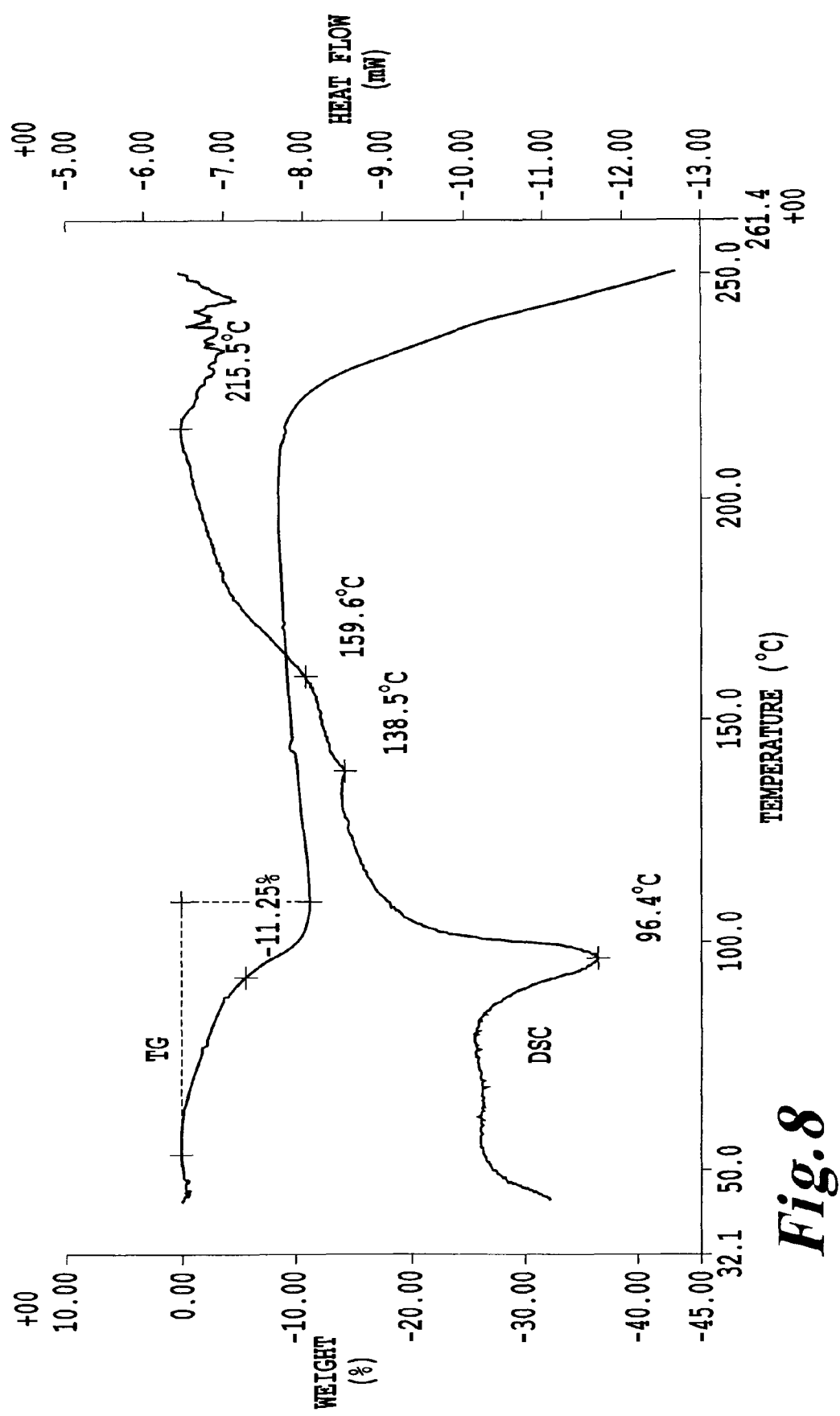
FIG. 8 shows the results of TG-DSC measurements of 2-[4-[2-(benzimidazol-2-ylthio)ethyl]piperazin-1-yl]-N-[2,4-bis(methylthio)-6-methyl-3-pyridyl]acetamide monosulfate 4-water adduct.
Figure 9:
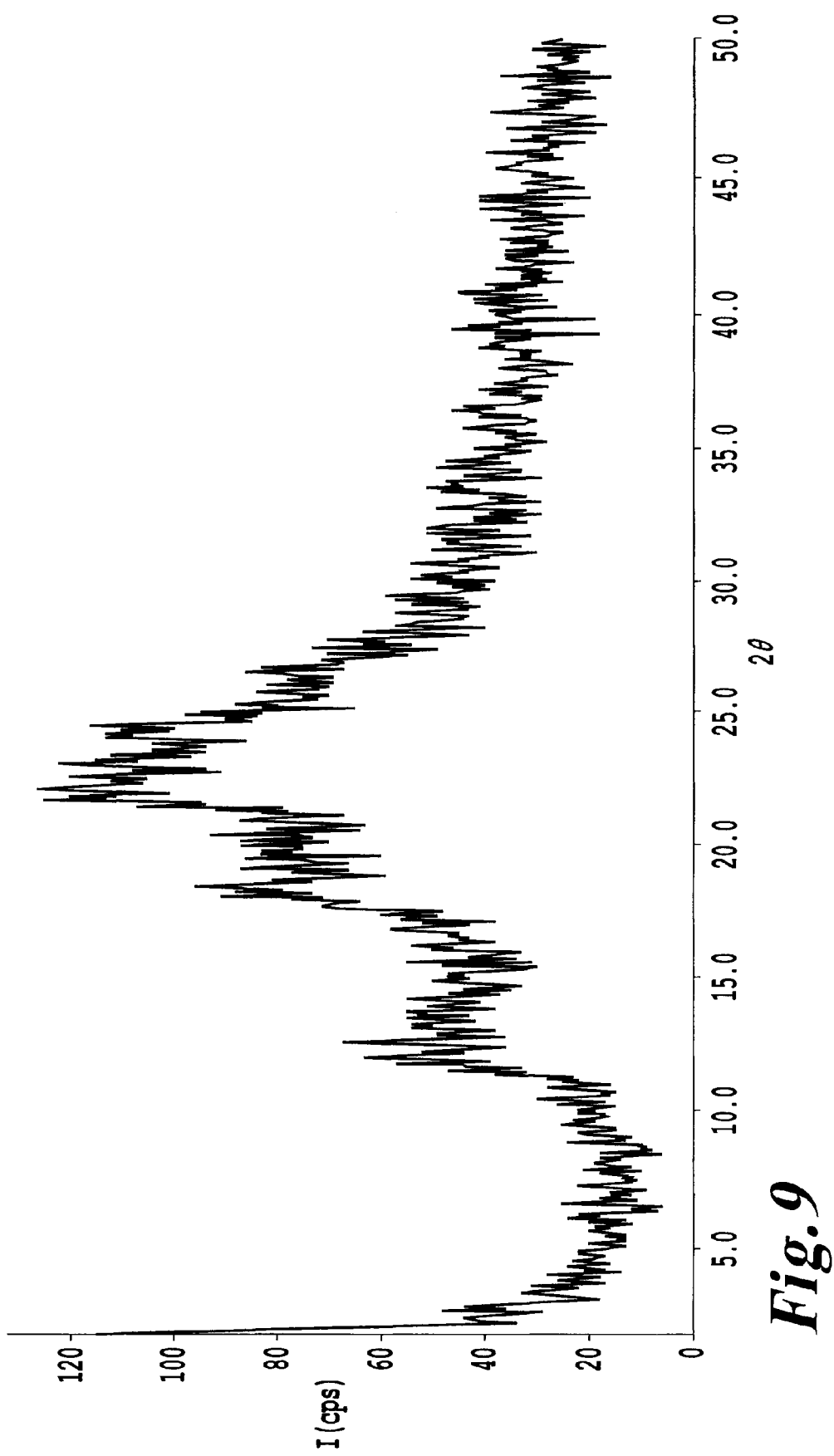
FIG. 9 shows a powder X-ray diffraction pattern of 2-[4-[2-(benzimidazol-2-ylthio)ethyl]piperazin-1-yl]-N-[2,4-bis(methylthio)-6-methyl-3-pyridyl]acetamide monosulfate.
Figure 10:
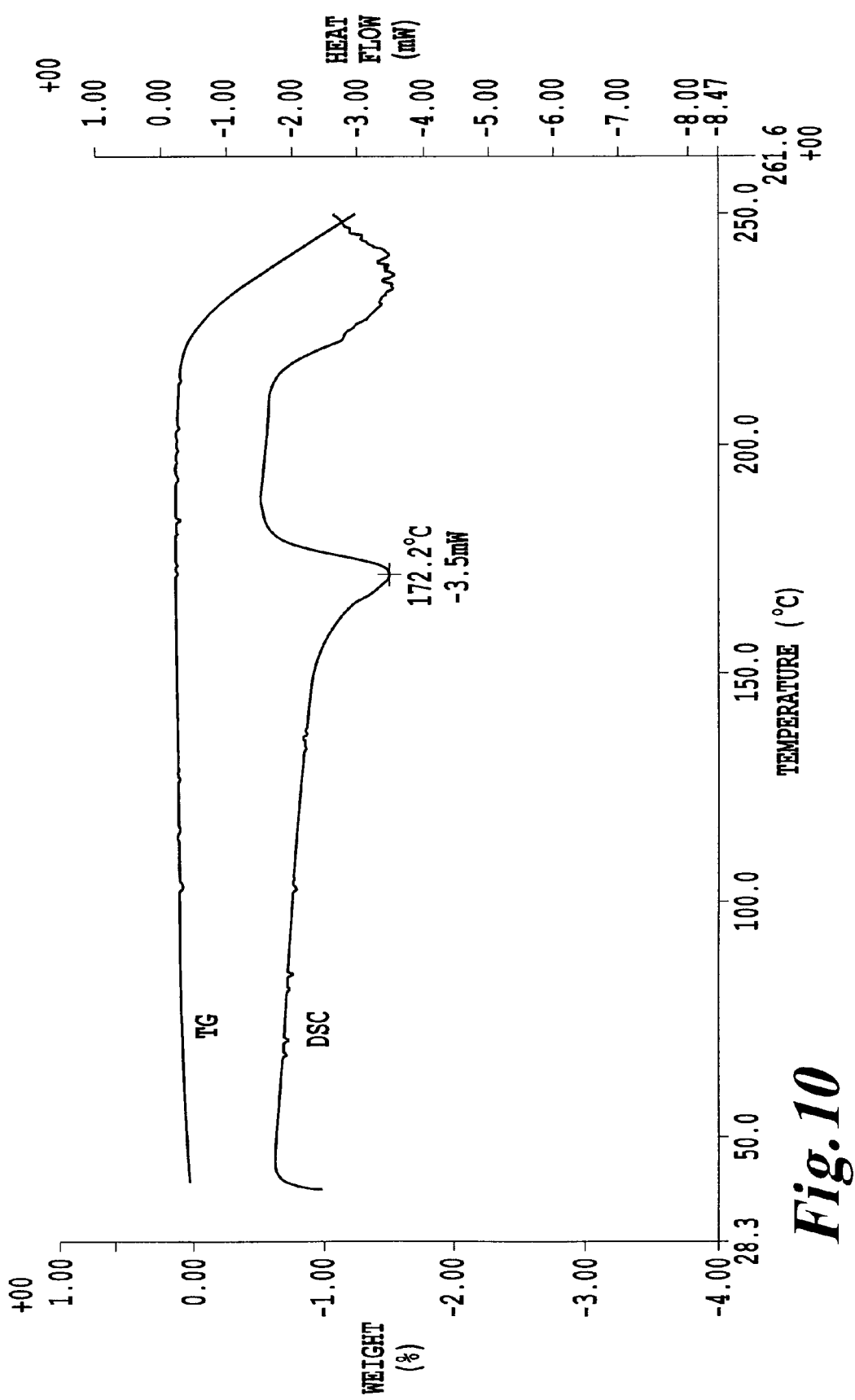
FIG. 10 shows the results of TG-DSC measurements of 2-[4-[2-(benzimidazol-2-ylthio)ethyl]piperazin-1-yl]-N-[2,4-bis(methylthio)-6-methyl-3-pyridyl]acetamide monosulfate.
Figure 11:
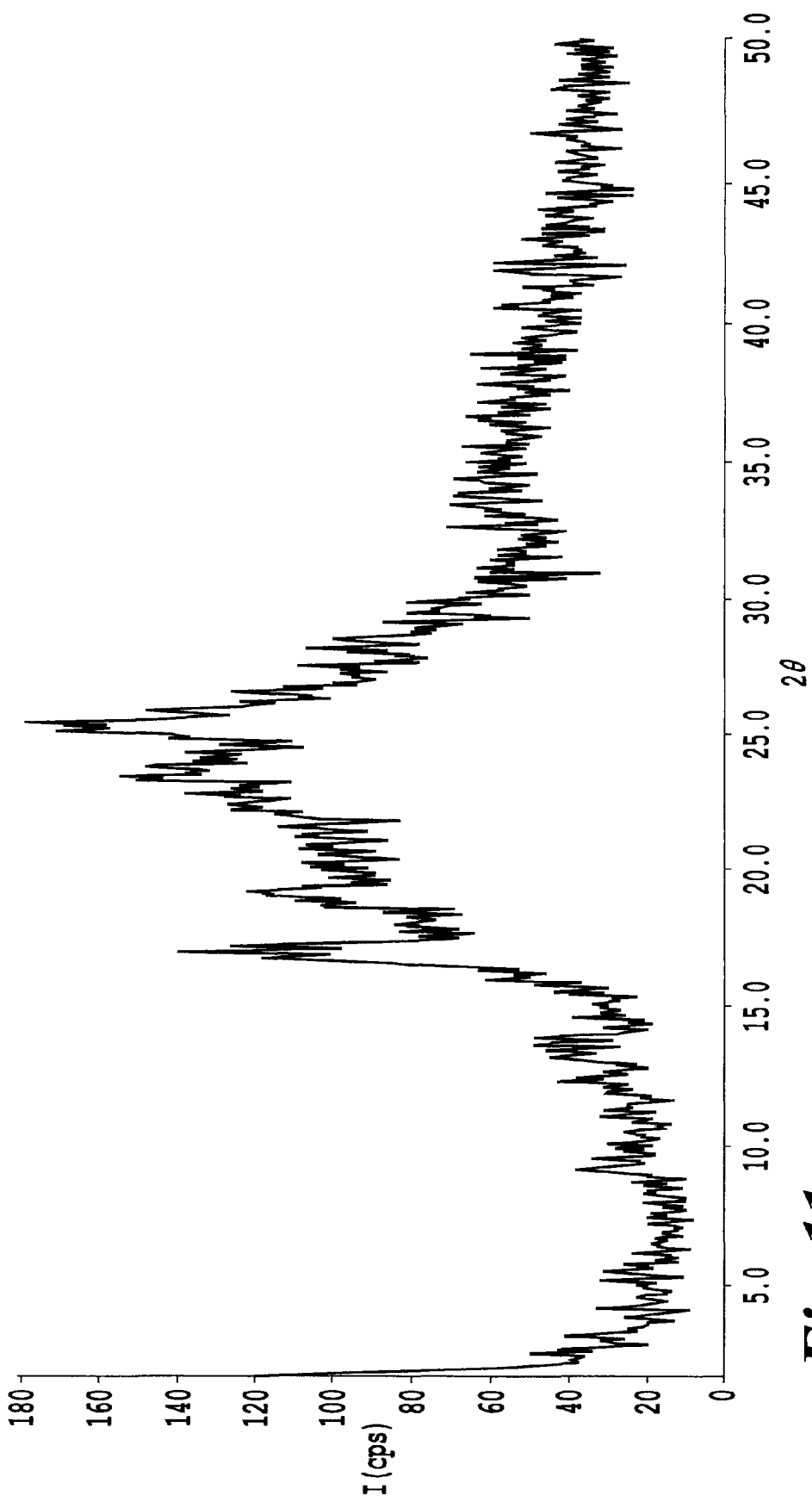
FIG. 11 shows a powder X-ray diffraction pattern of 2-[4-[2-(benzimidazol-2-ylthio)ethyl]piperazin-1-yl]-N-[2,4-bis(methylthio)-6-methyl-3-pyridyl]acetamide dimaleate.
Figure 12:
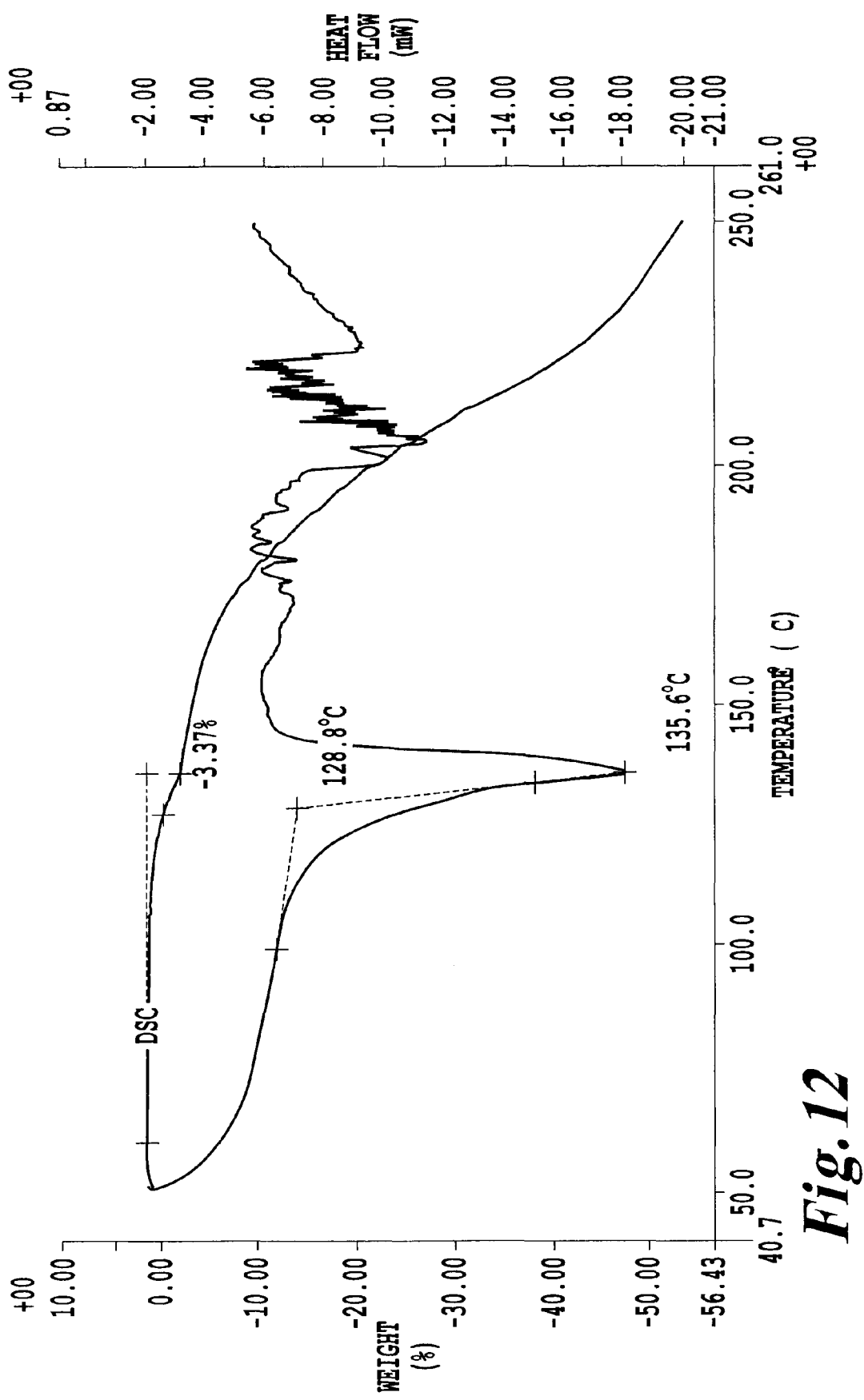
FIG. 12 shows the results of TG-DSC measurements of 2-[4-[2-(benzimidazol-2-ylthio)ethyl]piperazin-1-yl]-N-[2,4-bis(methylthio)-6-methyl-3-pyridyl]acetamide dimaleate.

A powder X-ray diffraction pattern of 2-[4-[2-(benzimidazol-2-ylthio)ethyl]piperazin-1-yl]-N-[2,4-bis(methylthio)-6-methyl-3-pyridyl]acetamide monohydrochloride 0.9-water adduct is illustrated in FIG. 1, and the results of its TG (thermogravimetric analysis)-DSC (differential scanning calorimetry) measurements are shown in FIG. 2. Further, a powder X-ray diffraction pattern of 2-[4-[2-(benzimidazol-2-ylthio)ethyl]piperazin-1-yl]-N-[2,4-bis(methylthio)-6-methyl-3-pyridyl]acetamide tetrahydrochloride 2-water adduct is illustrated in FIG. 3, and the results of its TG-DSC measurements are shown in FIG. 4. A powder X-ray diffraction pattern of 2-[4-[2-(benzimidazol-2-ylthio)ethyl]piperazin-1-yl]-N-[2,4-bis(methylthio)-6-methyl-3-pyridyl]acetamide disulfate 1.5-water adduct is illustrated in FIG. 5, and the results of its TG-DSC measurements are shown in FIG. 6. A powder X-ray diffraction pattern of 2-[4-[2-(benzimidazol-2-ylthio)ethyl]piperazin-1-yl]-N-[2,4-bis(methylthio)-6-methyl-3-pyridyl]acetamide monosulfate 4-water adduct is illustrated in FIG. 7, and the results of its TG-DSC measurements are shown in FIG. 8. A powder X-ray diffraction pattern of 2-[4-[2-(benzimidazol-2-ylthio)ethyl]piperazin-1-yl]-N-[2,4-bis(methylthio)-6-methyl-3-pyridyl]acetamide monosulfate is illustrated in FIG. 9, and the results of its TG-DSC measurements are shown in FIG. 10. A powder X-ray diffraction pattern of 2-[4-[2-(benzimidazol-2-ylthio)ethyl]piperazin-1-yl]-N-[2,4-bis(methylthio)-6-methyl-3-pyridyl]acetamide dimaleate is illustrated in FIG. 11, and the results of its TG-DSC measurements are shown in FIG. 12.

Example 2

Preparation of 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide monohydrochloride (1) Preparation of 1-tert-butoxycarbonyl-4-[2-(5,6-difluorobenzimidazol-2-ylthio)ethyl]piperazine To a solution of 1-tert-butoxycarbonyl-4-(2-hydroxyethyl)piperazine (7.40 g, 32.13 mmol) in THF (100 mL), triethylamine (4.36 g, 43.09 mmol), 4-dimethylaminopyridine (200 mg, 1.64 mmol) and methanesulfonyl chloride (7.40 g, 38.76 mmol) were successively added under ice cooling and stirring. The temperature of the reaction mixture was allowed to rise to room temperature, at which the reaction mixture was stirred for 50 minutes. The reaction mixture was filtered, and the filtrate was concentrated under reduced pressure. The residue was dissolved in DMF (200 mL). At room temperature, 5,6-difluoro-2-mercaptobenzimidazole (5.00 g, 26.86 mmol), potassium carbonate (8.64 g, 62.51 mmol) and 18-crown-6 (500 mg, 1.92 mmol) were successively added, followed by stirring at 80° C. for 90 minutes. The reaction mixture was concentrated under reduced pressure, and the residue was purified by column chromatography on silica gel (silica gel: 200 g; developer: hexane:acetone=8:1→1:1). Crystallization was conducted from acetone-ethyl ether-hexane to obtain the title compound (7.26 g, yield: 680) as colorless crystals.

Melting point: 192.3-193.0° C.
IR(KBr)cm$^{-1}$: 3061, 2976, 2836, 1672, 1475, 1427.
$^1$H-NMR (400 MHz, CDCl$_3$) δ: 1.50 (9H, s), 2.51-2.68 (4H, m), 2.94 (2H, t, J=5.4 Hz), 3.28 (2H, t, J=5.4 Hz), 3.45-3.65 (4H, m), 6.85-7.62 (2H, m).

TABLE 1

|  | Invention | Comparative Examples | | | | |
|---|---|---|---|---|---|---|
|  | Hydrochloride | Hydrochloride | Sulfates | | | Maleate |
|  | Salt | | | | | |
|  | Monohydrochloride 0.9-water adduct | Tetrahydrochloride 2-water adduct | Disulfate 1.5-water adduct | Monosulfate 4-water adduct | Monosulfate | Dimaleate |
| Solubility mg/mL | 0.5 | >1000 | >1000 | 5 | 200 (5 when left over) | 15 |
| pH of 1% aq. Solution | 5.2 (0.05%) | 1.97 | 2.00 | 3.2 (0.5%) | 3.2 (0.5%) | 2.62 |
| Melting point (° C.) | 194-196 | 193-196 | 204-208 | Unspecified | 170-171 | 127-130 |
| Thermal stability | 99.2% | 98.5% | 99.6% | 99.4% | (Not measured) | 93.1% |
| Hygro-scopicity | None | 10% | 10% | None | 15% | 2% |
| Powder X-ray | Crystallinity | Low crystallinity | Low crystallinity | Crystallinity | Low crystallinity | Low crystallinity |
| TG | No change until decomposition | Gradual removal of water and HCl | No change until decomposition | Decreased 10% at 100° C. and lower | No change until decomposition | Removal of water of crystallization |
| DSC | 1 peak at 194° C. | 1 peak at 188° C. | 2 peaks at 168 and 210° C. | 3 peaks at 95, 168 and 210° C. | 1 peak at 172° C. | 2 peaks at 117 and 137° C. |

(Note)
Thermal stability: The purity of each acid addition salt of the polyacidic basic compound stored at 80° C. for 10 days was determined by HPLC measurement relative to its purity before the storage with the proviso that the disulfate 1.5-water adduct and the dimaleate were stored at 60° C. for 7 days before their storage at 80° C. for 10 days.
Hygroscopicity: A weight change of each acid addition salt was measured after storing it for 4 days under conditions of 25° C. and 83% relative humidity.
TG: Thermogravimetric analysis
DSC: Differential scanning calorimetry As being evident from Table 1, 2-[4-[2-(benzimidazol-2-ylthio)ethyl]piperazin-1-yl]-N-[2,4-bis(methylthio)-6-methyl-3-pyridyl]acetamide monohydrochloride 0.9-water adduct according to the present invention had a high degree of crystallinity, had no hygroscopicity, was excellent in thermal stability without any substantial weight change resulting from dehydration, dehydrochlorination and/or the like, did not develop the problem of polymorphism, was free from the influence of any residual of hydrochloric acid, and therefore, was a preferred acid addition salt.

(2) Preparation of 1-[2-(5,6-difluorobenzimidazol-2-ylthio)ethyl]piperazine tritrifluoroacetate 1-tert-Butoxycarbonyl-4-[2-(5,6-difluorobenzimidazol-2-ylthio)ethyl]piperazine (7.26 g, 18.22 mmol) was added to trifluoroacetic acid (50 mL) over 15 minutes under ice cooling and stirring to dissolve the same. Subsequent to stirring for 10 minutes under ice cooling, ether (100 mL) and hexane (100 mL) were added to the reaction mixture and crystals were collected by filtration. The crystals were recrystallized from ethanol-diethyl ether to afford the title compound (9.58 g, yield: 82%) as a pale yellow powder.

Melting point: 141.2-142.9° C.
IR(KBr)cm$^{-1}$: 3417, 3026, 2749, 2483, 1671, 1484.
$^1$H-NMR (400 MHz, DMSO-d$_6$) δ: 2.78-3.26 (10H, m), 3.49 (2H, t, J=7.2 Hz), 7.51 (2H, t, J=9.0 Hz), 8.76 (2H, m).

(3) Preparation of 2,4-bis(2,2,2-trifluoroethoxy)-6-methyl-3-nitropyridine 2,4-Dichloro-6-methyl-3-nitropyridine (30 g, 144.9 mmol) was dissolved in 2,2,2-trifluoroethanol (250 mL), followed by the addition of potassium carbonate (50 g, 361.8 mmol). The mixture was subjected to heating under reflux for 21 hours. The reaction mixture was extracted with chloroform-water. The organic layer was washed with a saturated aqueous solution of sodium chloride (brine), dried over anhydrous sodium sulfate, and concentrated under reduced pressure to obtain the title compound (45.40 g, 94%) as a pale yellow oil.

Melting point: 72.8-73.2° C.
IR(KBr)cm$^{-1}$: 3432, 3111, 2975, 1610, 1585, 1535.
$^1$H-NMR (400 MHz, CDCl$_3$) δ: 2.50 (3H, s), 4.49 (2H, q, J=7.7 Hz), 4.85 (2H, q, J=8.3 Hz), 6.53 (1H, s).
Elemental analysis for C$_{10}$H$_8$F$_6$N$_2$O$_4$:
Calculated: C, 35.94; H, 2.41; N, 8.38
Found: C, 35.94; H, 2.45; N, 8.49

(4) Preparation of 3-amino-2,4-bis(2,2,2-trifluoroethoxy)-6-methylpyridine 2,4-Bis(2,2,2-trifluoroethoxy)-6-methyl-3-nitropyridine (45.00 g, 134.7 mmol) was dissolved in isopropanol (300 mL). While stirring the solution at 80° C., a solution of sodium dithionite (78.00 g, 448.0 mmol) in water (300 mL) was added, followed by stirring for 15 minutes. A solution of sodium dithionite (16.50 g, 94.8 mmol) in water (51 mL) was added, and the mixture was stirred for 10 minutes. Further, a solution of sodium dithionite (11.10 g, 63.8 mmol) in water (51 mL) was added, followed by stirring for 10 minutes. A 4 mol/L aqueous solution of sulfuric acid (201 mL) was added, and the mixture was stirred at 90° C. for 30 minutes. After allowing the reaction mixture to cool down to room temperature, 28% aqueous ammonia (310 mL) was added to the reaction mixture in an ice bath, followed by stirring for 30 minutes. The mixture was extracted with chloroform. The organic layer was washed with brine, dried over anhydrous sodium sulfate, and concentrated under reduced pressure. The residue was recrystallized from hexane to obtain the title compound (32.91 g, 80%) as pale yellow needles.

Melting point: 53.5-53.8° C.
IR(KBr)cm$^{-1}$: 3453, 3314, 2968, 1603, 1505, 1456.
$^1$H-NMR (400 MHz, CDCl$_3$) δ: 2.34 (3H, s), 3.66 (2H, br s), 4.39 (2H, q, J=8.0 Hz), 4.79 (2H, q, J=8.6 Hz), 6.35 (1H, s).
Elemental analysis for C$_{10}$H$_{10}$F$_6$N$_2$O$_2$·0.55H$_2$O:
Calculated: C, 38.24; H, 3.56; N, 8.92
Found: C, 37.96; H, 3.19; N, 8.94

(5) Preparation of 2-bromo-N-[2,4-bis(2,2,2-trifluoroethoxy)-6-methyl-3-pyridyl]acetamide 3-Amino-2,4-bis(2,2,2-trifluoroethoxy)-6-methyl-3-nitropyridine (42.29 g, 139.0 mmol) was dissolved in dichloromethane (600 mL), followed by the addition of N,N-dimethylaniline (20.46 g, 16.8 mmol). While stirring the mixture in an ice bath, a solution of bromoacetyl bromide (28.73 g, 142.3 mmol) in dichloromethane (100 mL) was added dropwise, and the reaction mixture was stirred at room temperature for 10 minutes. The reaction mixture was extracted with chloroform-water. The organic layer was washed with brine, dried over anhydrous sodium sulfate, and concentrated under reduced pressure. The residue was recrystallized from chloroform-hexane to obtain the title compound (50.25 g, 85%) as colorless needles.

Melting point: 152.8-154.0° C.
IR(KBr)cm$^{-1}$: 3250, 3053, 1677, 1597, 1541, 1456.
$^1$H-NMR (400 MHz, CDCl$_3$) δ: 2.43 (3H, s), 4.02 (2H, s), 4.42 (2H, q, J=7.9 Hz), 4.78 (2H, q, J=8.5 Hz), 6.47 (1H, s), 7.49 (1H, br s).
Elemental analysis for C$_{12}$H$_{11}$BrF$_6$N$_2$O$_3$:
Calculated: C, 33.90; H, 2.61; N, 6.59
Found: C, 34.13; H, 2.66; N, 6.65

(6) Preparation of 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide To a mixed solution of 1-[2-(5,6-difluorobenzimidazol-2-ylthio)ethyl]piperazine tritrifluoroacetate (4.00 g, 6.25 mmol) and potassium carbonate (4.32 g, 31.26 mmol) in acetonitrile (100 mL) and water (30 mL), 2-bromo-N-[2,4-bis(2,2,2-trifluoroethoxy)-6-methyl-3-pyridyl]acetamide (2.20 g, 5.22 mmol) was added over 15 minutes under ice cooling and stirring. After stirring the reaction mixture at room temperature for 15 hours, it was extracted with chloroform-water. The organic layer was washed with brine, dried over anhydrous sodium sulfate, and concentrated under reduced pressure. The residue was purified by column chromatography (silica gel; 150 g; developer: hexane: acetone=Recrystallization was conducted from chloroform-hexane to obtain the title compound (3.04 g, 91%) as a pale yellow powder.

Melting point: 191-192° C.
IR(KBr)cm$^{-1}$: 3275, 1686, 1604, 1591, 1509.
$^1$H-NMR (400 MHz, DMSO-d$_6$) δ: 2.38 (3H, s), 2.42-2.62 (8H, m), 2.67 (2H, t, J=6.7 Hz), 3.30 (2H, s), 3.40 (2H, t, J=6.7 Hz), 4.82 (2H, q, J=8.8 Hz), 4.90 (2H, q, J=8.8 Hz), 6.91 (1H, s), 7.47 (2H, m), 8.77 (1H, s), 12.82 (1H, br s).
Elemental analysis for C$_{25}$H$_{26}$F$_8$N$_6$O$_3$S:
Calculated: C, 46.73; H, 4.08; N, 13.08
Found: C, 46.55; H, 4.12; N, 12.94

(7) Preparation of 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide hydrochloride After dissolving 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide (1.00 g, 1.56 mmol) in ethanol (20 mL), pyridine hydrochloride (360 mg, 3.12 mmol) was added. The reaction mixture was concentrated, and the residue was recrystallized from ethanol to obtain the title compound (787 mg, 78%; including 40% equivalent of ethanol as determined by $^1$H-NMR) as a colorless crystalline powder.

(8) The crystalline powder (300 mg) prepared in the procedure (7) was suspended in water (3 mL), followed by heating under reflux for 1 hour. After allowing the reaction mixture to cool down to room temperature, crystals were collected by filtration, washed with water (2 mL×2), and heated and dried at 50° C. for 7 hours under reduced pressure to obtain the title compound (144 mg, 48%) in an ethanol-free form as a colorless crystalline powder.

Figure 13:
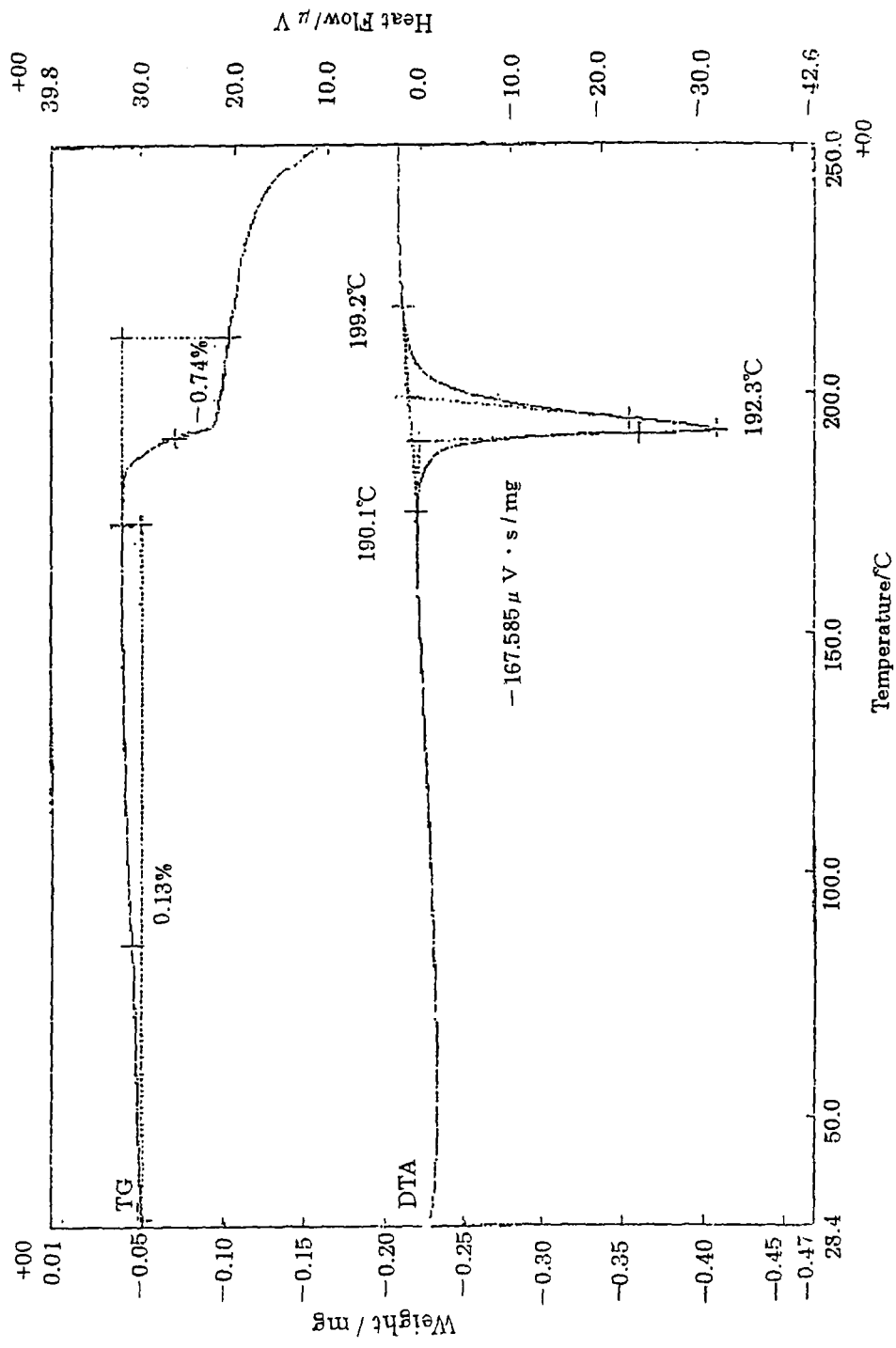
FIG. 13 and FIG. 14 show a diagram showing the results of TG-DTA measurements of 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide and its monohydrochloride, respectively.
Figure 14:
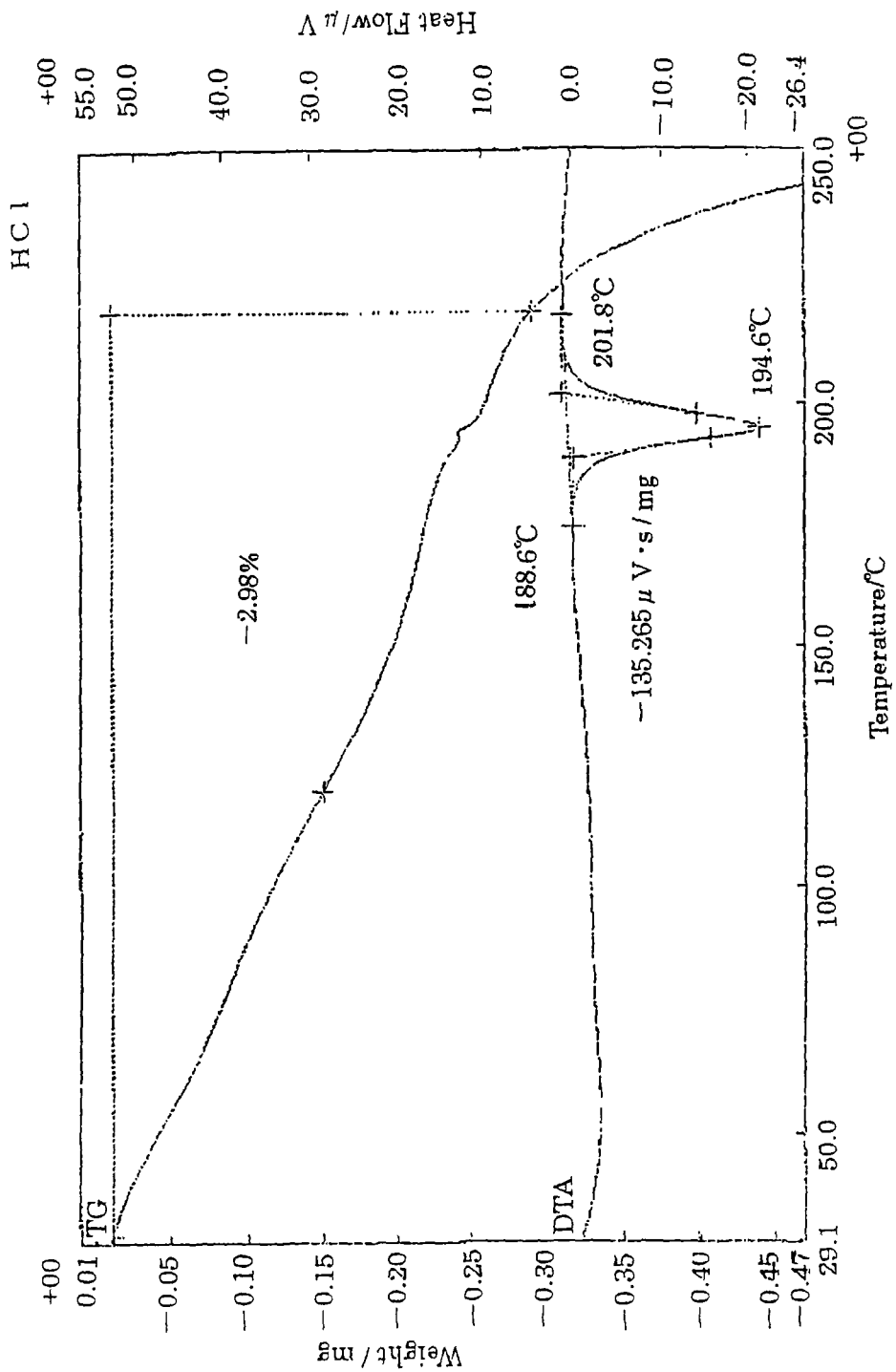

FIG. 13 and FIG. 14 show the results of TG (thermogravimetric analysis)-DTA (differential thermal analysis) measurements of 2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide and its monohydrochloride, respectively.

Melting point: 186-187° C.
IR(KBr)cm$^{-1}$: 3389, 3263, 1686, 1592, 1514, 1479, 1274.
$^1$H-NMR (400 MHz, DMSO-d$_6$) δ: 2.41 (3H, s), 2.80-3.74 (14H, m), 4.87 (2H, q, J=8.8 Hz), 4.94 (2H, q, J=9.0 Hz), 6.96 (1H, s), 7.50 (2H, t, J=9.0 Hz), 9.11 (1H, br).
Elemental analysis for $C_{25}H_{27}ClF_8N_6O_3S\cdot1.6H_2O$:
Calculated: C, 42.42; H, 4.30; N, 11.87; Cl, 5.01
Found: C, 42.72; H, 4.62; N, 11.23; Cl, 4.98

Example 3

Preparation of 2-[4-[2-(benzimidazol-2-ylthio)ethyl]piperazin-1-yl]-N-[2,4-bis(2,2,2-trifluoroethoxy)-6-methyl-3-pyridyl]acetamide dihydrochloride (1) Preparation of 2-[4-[2-(benzimidazol-2-ylthio)ethyl]piperazin-1-yl]-N-[2,4-bis(2,2,2-trifluoroethoxy)-6-methyl-3-pyridyl]acetamide In a procedure similar to that described in Example 2 except for the use of 1-[2-(benzimidazol-2-ylthio)ethyl]piperazine trihydrochloride in place of 1-[2-(5,6-difluorobenzimidazol-2-ylthio)ethyl]piperazine tritrifluoroacetate, the title compound (91%) was obtained as a colorless crystalline powder.

Melting point: 152-153° C.
$^1$H-NMR (400 MHz, CDCl$_3$) δ: 2.43 (3H, s), 2.65-2.97 (8H, m), 3.01 (2H, t, J=5.0 Hz), 3.23 (2H, t, J=5.0 Hz), 3.31 (2H, s), 4.42 (2H, q, J=8.0 Hz), 4.75 (2H, q, J=8.5 Hz), 6.48 (1H, s), 7.60-7.24 (2H, m), 7.41-7.65 (2H, m), 8.26 (1H, s).

(2) Preparation of 2-[4-[2-(benzimidazol-2-ylthio)ethyl]piperazin-1-yl]-N-[2,4-bis(2,2,2-trifluoroethoxy)-6-methyl-3-pyridyl]acetamide dihydrochloride After dissolving the free base (1.00 g, 1.65 mmol) of 2-[4-[2-(benzimidazol-2-ylthio)ethyl]piperazin-1-yl]-N-[2,4-bis(2,2,2-trifluoroethoxy)-6-methyl-3-pyridyl]acetamide in ethanol (20 mL), pyridine hydrochloride (381 mg, 3.30 mmol) was added. The reaction mixture was concentrated, and to the residue, ethanol (0.5 mL) and water (5 mL) were added.

A precipitate was collected by filtration to obtain 2-[4-[2-(benzimidazol-2-ylthio)ethyl]piperazin-1-yl]-N-[2,4-bis(2,2,2-trifluoroethoxy)-6-methyl-3-pyridyl]acetamide dihydrochloride (545 mg, 52%) as a colorless crystalline powder. The dihydrochloride (250 mg) was suspended in water (2.5 mL), followed by heating to 80° C. to dissolve the same. After allowing the reaction mixture to cool down to room temperature, crystals were collected by filtration, washed with water (1 mL×2), and heated and dried at 50° C. for 7 hours under reduced pressure to obtain the title compound (183 mg, 73%) as a colorless crystalline powder.

Figure 15:
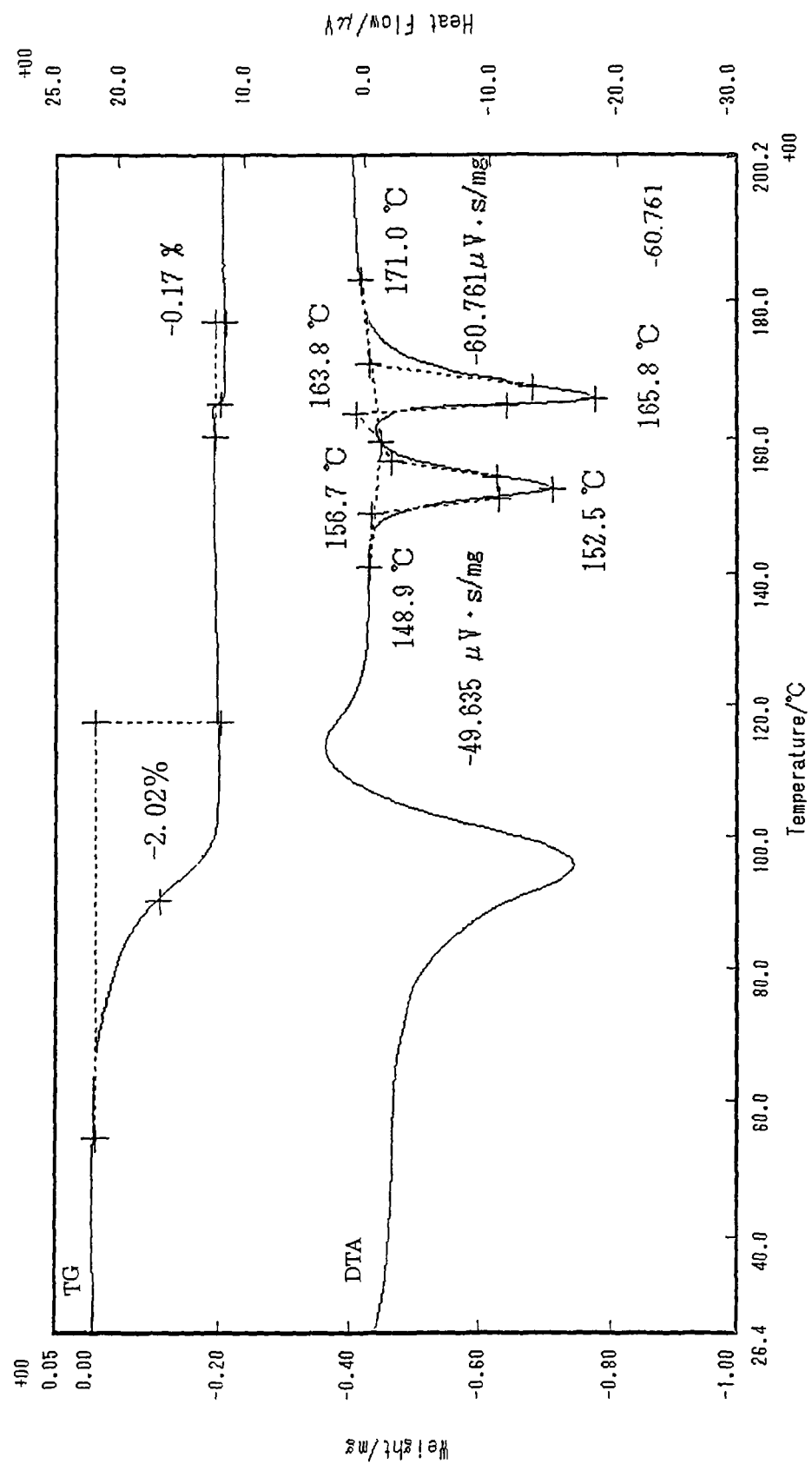
FIG. 15 and FIG. 16 show the results of TG-DTA measurements of 2-[4-[2-(benzimidazol-2-ylthio)ethyl]piperazin-1-yl]-N-[2,4-bis(2,2,2-trifluoroethoxy)-6-methyl-3-pyridyl]acetamide and its dihydrochloride, respectively.
Figure 16:
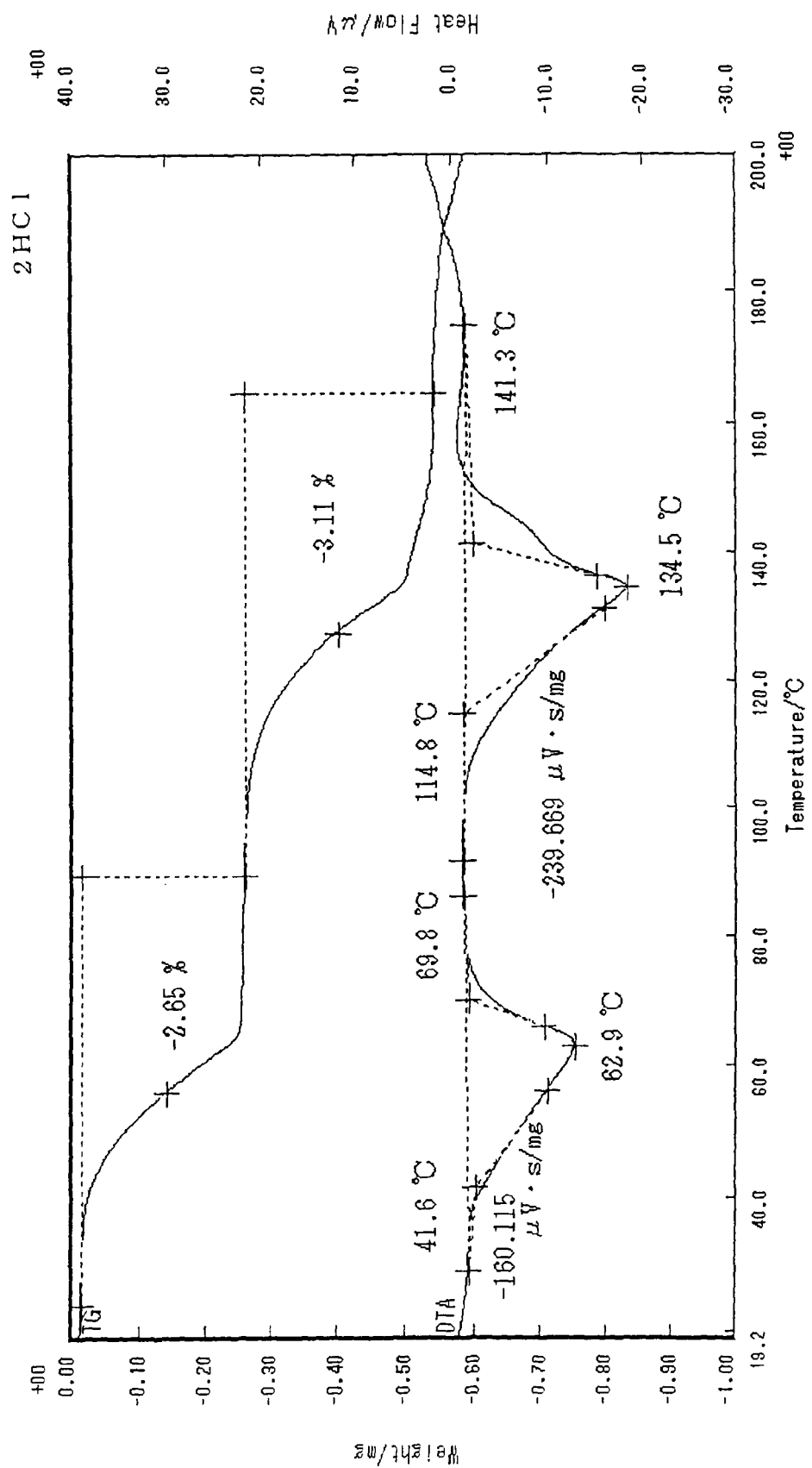

FIG. 15 and FIG. 16 show the results of TG-DTA measurements of 2-[4-[2-(benzimidazol-2-ylthio)ethyl]piperazin-1-yl]-N-[2,4-bis(2,2,2-trifluoroethoxy)-6-methyl-3-pyridyl]acetamide and its dihydrochloride, respectively.

Melting point: 153-154° C.
IR(KBrcm$^{-1}$): 3407, 1691, 1592, 1513, 1274, 1168.
$^1$H-NMR (400 MHz, CD$_3$CN) δ: 2.40 (3H, s), 2.90-3.19 (4H, m), 3.26 (2H, s), 3.27-3.42 (4H, m), 3.46 (2H, t, J=7.1 Hz), 3.81 (2H, t, J=7.1 Hz), 4.57 (2H, q, J=8.3 Hz), 4.83 (2H, q, J=8.8 Hz), 6.71 (1H, s), 7.34 (2H, dd, J=3.2, 6.1 Hz), 7.64 (2H, dd, J=3.2, 6.1 Hz), 8.31 (1H, br).
Elemental analysis for $C_{25}H_{30}Cl_2F_6N_6O_3S\cdot1.3H_2O$:
Calculated: C, 42.72; H, 4.67; N, 11.96; Cl, 10.09
Found: C, 42.73; H, 4.88; N, 11.86; Cl, 10.01

Example 4

Preparation of 2-[4-[2-(benzoxazol-2-ylthio)ethyl]piperazin-1-yl]-N-[2,4-bis(2,2,2-trifluoroethoxy)-6-methyl-3-pyridyl]acetamide monohydrochloride (1) Preparation of 2-[4-[2-(benzoxazol-2-ylthio)ethyl]piperazin-1-yl]-N-[2,4-bis(2,2,2-trifluoroethoxy)-6-methyl-3-pyridyl]acetamide By conducting a reaction and treatments similar to those described in Example 3 except for the use of 1-[2-(benzoxazol-2-ylthio)ethyl]piperazine ditrifluoroacetate in place of 1-[2-(benzimidazol-2-ylthio)ethyl]piperazine trihydrochloride, the title compound was obtained.

Melting point: 141-142° C.
$^1$HNMR (400 MHz, CDCl$_3$) δ: 2.42 (3H, s), 2.54-2.76 (8H, m), 2.84 (2H, t, J=6.9 Hz), 3.15 (2H, s), 3.49 (2H, t, J=6.9 Hz), 4.41 (2H, q, J=8.0 Hz), 4.75 (2H, q, J=8.5 Hz), 6.46 (1H, s), 7.25-7.35 (2H, m), 7.43 (1H, d, J=7.8 Hz), 7.59 (1H, d, J=7.8 Hz), 8.38 (1H, s).

(2) Preparation of 2-[4-[2-(benzoxazol-2-ylthio)ethyl]piperazin-1-yl]-N-[2,4-bis(2,2,2-trifluoroethoxy)-6-methyl-3-pyridyl]acetamide monohydrochloride After dissolving of 2-[(4-[2-(benzoxazol-2-ylthio)ethyl]piperazin-1-yl]-N-[2,4-bis(2,2,2-trifluoroethoxy)-6-methyl-3-pyridyl]acetamide (1.00 g, 1.65 mmol) in ethanol (20 mL), pyridine hydrochloride (380 mg, 3.29 mmol) was added. The reaction mixture was concentrated, and to the residue, ethanol (0.5 mL) and water (5 mL) were added. A precipitate was collected by filtration to obtain 2-[4-[2-(benzoxazol-2-ylthio)ethyl]piperazin-1-yl]-N-[2,4-bis(2,2,2-trifluoroethoxy)-6-methyl-3-pyridyl]acetamide monohydrochloride (786 mg, 74%) as a colorless crystalline powder. The monohydrochloride (300 mg) was suspended in water (1.5 mL), followed by heating to 80° C. to dissolve the same. After allowing the reaction mixture to cool down to room temperature, crystals were collected by filtration, washed with water (0.5 mL×2), and heated and dried at 50° C. for 7 hours under reduced pressure to obtain the title compound (84 mg, 28%) as a colorless crystalline powder.

Figure 17:
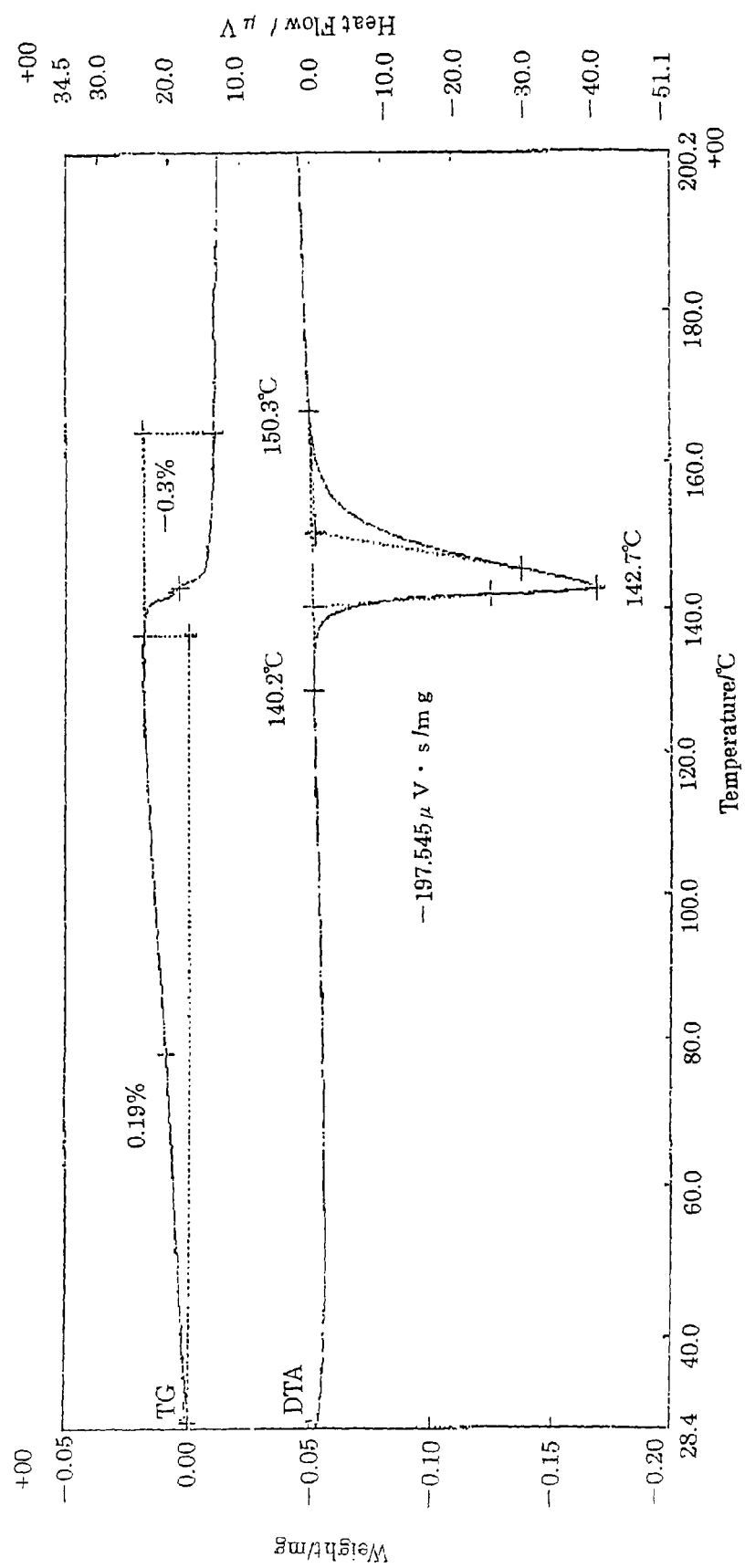
FIG. 17 and FIG. 18 show the results of TG-DTA measurements of 2-[4-[2-(benzoxazol-2-ylthio)ethyl]piperazin-1-yl]-N-[2,4-bis(2,2,2-trifluoroethoxy)-6-methyl-3-pyridyl]acetamide and its monohydrochloride, respectively.
Figure 18:
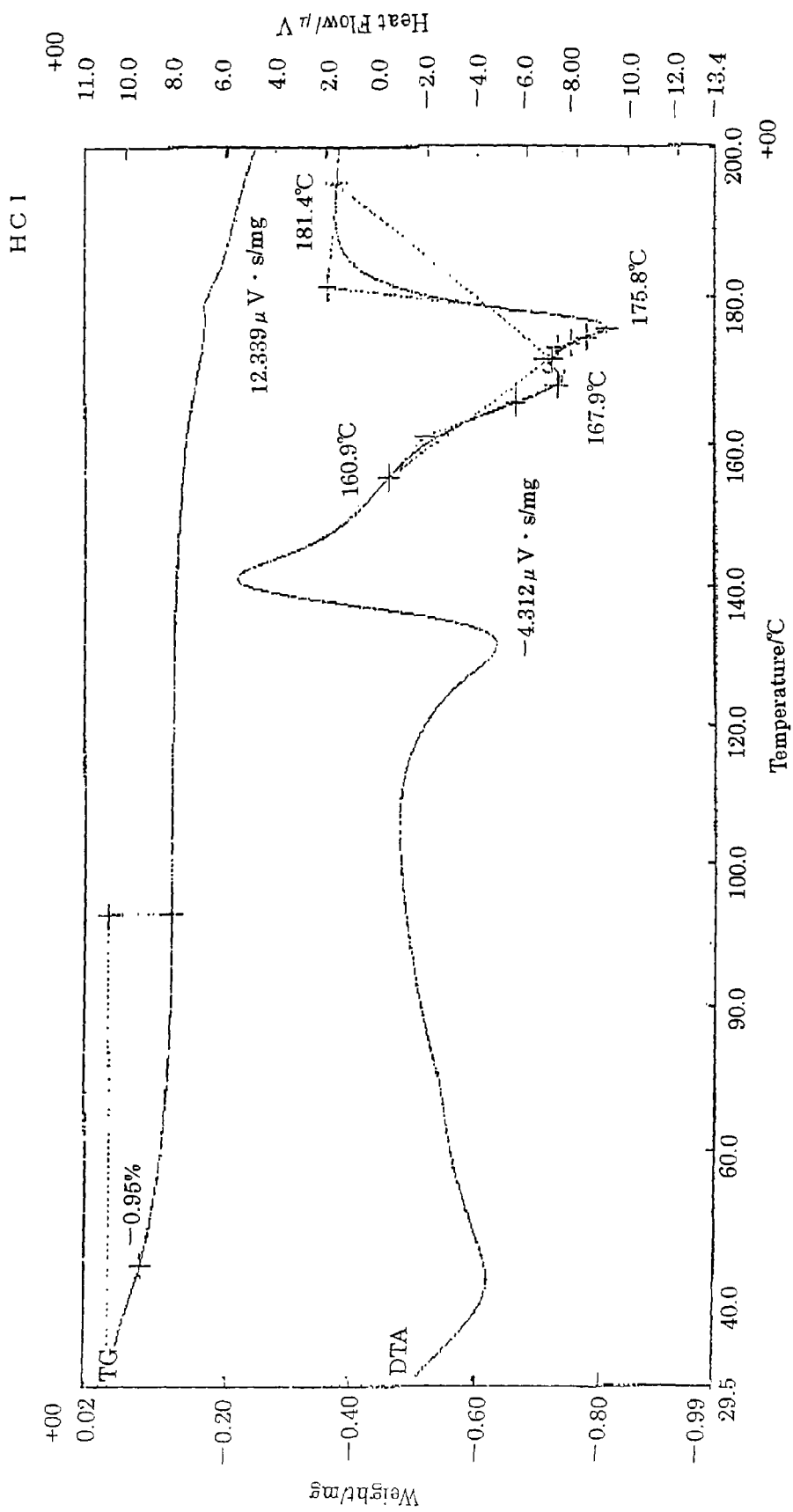

FIG. 17 and FIG. 18 show the results of TG-DTA measurements of 2-[4-[2-(benzoxazol-2-ylthio)ethyl]piperazin-1-yl]-N-[2,4-bis(2,2,2-trifluoroethoxy)-6-methyl-3-pyridyl]acetamide and its monohydrochloride, respectively.

Melting point: 174-176° C.

IR(KBr)cm$^{-1}$: 3431, 1690, 1591, 1508, 1454, 1274, 1169, 1139.

$^1$H-NMR (400 MHz, DMSO-d$_6$) δ: 2.39 (3H, s), 2.66-3.82 (14H, m), 4.87 (2H, q, J=8.5 Hz), 4.94 (2H, q, J=9.0 Hz), 6.96 (1H, s), 7.33 (2H, t, J=3.4 Hz), 7.60-7.69 (2H, m), 8.17 (1H, br).

Elemental analysis for C$_{25}$H$_{28}$ClF$_6$N$_5$O$_4$S.0.4H$_2$O:

Calculated: C, 46.11; H, 4.46; N, 10.75; Cl, 5.44.

Found: C, 46.17; H, 4.44; N, 10.74; Cl, 5.30.

Example 5

Preparation of 2-[4-[2-(benzothiazol-2-ylthio)ethyl]piperazin-1-yl]-N-[2,6-dimethyl-4-trifluoromethyl-3-pyridyl]acetamide dihydrochloride (1) Preparation of methyl 2,6-dimethyl-4-trifluoromethylpyridine-3-carboxylate 1,1,1-Trifluoro-2,4-pentanedione (25.01 g, 135.3 mmol) was dissolved in acetonitrile (230 mL), followed by the addition of methyl 3-aminocrotonate (15.57 g, 135.2 mmol). The mixture was subjected to heating under reflux for 20 hours. The reaction mixture was allowed to cool down to room temperature, and concentrated under reduced pressure. The residue was purified by column chromatography on silica gel (silica gel: 400 g; developer: hexane:acetone=10:1) to obtain the title compound (22.30 g, 71%) as a yellow oil.

(2) Preparation of 2,6-dimethyl-4-trifluoromethylpyridine-3-carboxylic acid hydrochloride Methyl 2,6-dimethyl-4-trifluoromethylpyridine-3-carboxylate (23.30 g, 99.9 mmol) was dissolved in ethanol (50 mL), followed by the addition of 5 mol/L aqueous solution of potassium hydroxide (50 mL, 250 mmol). The mixture was subjected to heating under reflux for 2 days. The reaction mixture was allowed to cool down to room temperature, and concentrated hydrochloric acid (15 mL) was added and concentrated under reduced pressure. The residue was azeotropically distilled three times with ethanol and toluene. The residue was suspended in ethanol under heat, and subsequent to filtration, the filtrate was concentrated under reduced pressure. The residue was azeotropically distilled twice with toluene, and subsequent to the addition of ether, the reaction product was collected by filtration to obtain the title compound (25.24 g, 99%) as a colorless powder.

(3) Preparation of 3-tert-butoxycarbonylamino-2,6-dimethyl-4-trifluoromethylpyridine 2,6-Dimethyl-4-trifluoromethylpyridine-3-carboxylic acid hydrochloride (23.17 g, 90.6 mmol) was suspended in tert-butanol (175 mL), and subsequent to the addition of Diphenylphosphorylazide (DPPA) (35.25 g, 128.1 mmol) and triethylamine (31.36 g, 309.9 mmol), the suspension was subjected to heating under reflux for 3 hours. Water (100 mL) was added to the reaction mixture, followed by extraction from chloroform. The organic layer was dried over anhydrous sodium sulfate, and concentrated under reduced pressure. The residue was purified by column chromatography on silica gel (silica gel: 400 g; developer: hexane:acetone=10:1) to obtain the title compound (18.01 g, 68%) as a pale yellow oil.

(4) Preparation of 3-amino-2,6-dimethyl-4-trifluoromethylpyridine dihydrochloride 3-tert-Butoxycarbonylamino-2,6-dimethyl-4-trifluoromethylpyridine (21.12 g, 72.8 mmol) was dissolved in methanol (70 mL), and subsequent to the addition of 10% hydrogen chloride in methanol (140 mL), the solution was stirred at 60° C. for 12 hours. The reaction mixture was concentrated under reduced pressure, and the residue was suspended in a mixture of ethyl acetate and ether. The reaction product was collected by filtration, and washed with ether to obtain the title compound (15.64 g, 82%) as a colorless powder.

(5) Preparation of 2-bromo-N-(2,6-dimethyl-4-trifluoromethyl-3-pyridyl)acetamide 3-Amino-2,6-dimethyl-4-trifluoromethylpyridine dihydrochloride (15.60 g, 59.30 mmol) was dissolved in methanol (100 mL). In an ice bath, an ammonia-saturated methanol solution (300 mL) was added, and the mixture was rendered uniform. The reaction mixture was extracted from chloroform-water. The organic layer was washed with brine, dried over anhydrous sodium sulfate, and concentrated under reduced pressure. The residue was dissolved in dichloromethane (200 mL), and subsequent to the addition of N,N-dimethylaniline (10.80 g, 89.12 mmol), a solution of bromoacetyl bromide (15.52 g, 76.90 mmol) in dichloromethane (40 mL) was added dropwise while stirring the mixture in an ice bath. The mixture was stirred at room temperature for two hours, and concentrated under reduced pressure. The residue was purified by column chromatography on silica gel (silica gel: 400 g; developer: hexane:acetone=10:1→4:1→3:1). Recrystallization from ethyl acetate and hexane afforded the title compound (17.68 g, 96%) as colorless needles.

(6) Preparation of 2-[4-[2-(benzothiazol-2-ylthio)ethyl]piperazin-1-yl]-N-[2,6-dimethyl-4-trifluoromethyl-3-pyridyl]acetamide The title compound was obtained as a free base by conducting a reaction and treatments similar to those described in Example 3 except that 2-bromo-N-(2,6-dimethyl-4-trifluoromethyl-3-pyridyl)acetamide was used in place of 2-bromo-N-[2,4-bis(2,2,2-trifluoroethoxy)-6-methyl-3-pyridyl]acetamide and 1-[2-(benzothiazol-2-ylthio)ethyl]piperazine dihydrochloride was used in lieu of 1-[2-(benzimidazol-2-ylthio)ethyl]piperazine trihydrochloride.

(7) Preparation of 2-[4-[2-(benzothiazol-2-ylthio)ethyl]piperazin-1-yl]-N-[2,6-dimethyl-4-trifluoromethyl-3-pyridyl]acetamide dihydrochloride 2-[4-[2-(benzothiazol-2-ylthio)ethyl]piperazin-1-yl]-N-[2,6-dimethyl-4-trifluoromethyl-3-pyridyl]acetamide (500 mg, 0.98 mmol) was dissolved in ethanol (10 mL), followed by the addition of pyridine hydrochloride (227 mg, 1.96 mmol). The reaction mixture was concentrated, and to the residue, ethanol (0.2 mL) and water (2 mL) were added. A precipitate was collected by filtration to obtain the title compound (295 mg, 55%) as a colorless crystalline powder.

Figure 19:
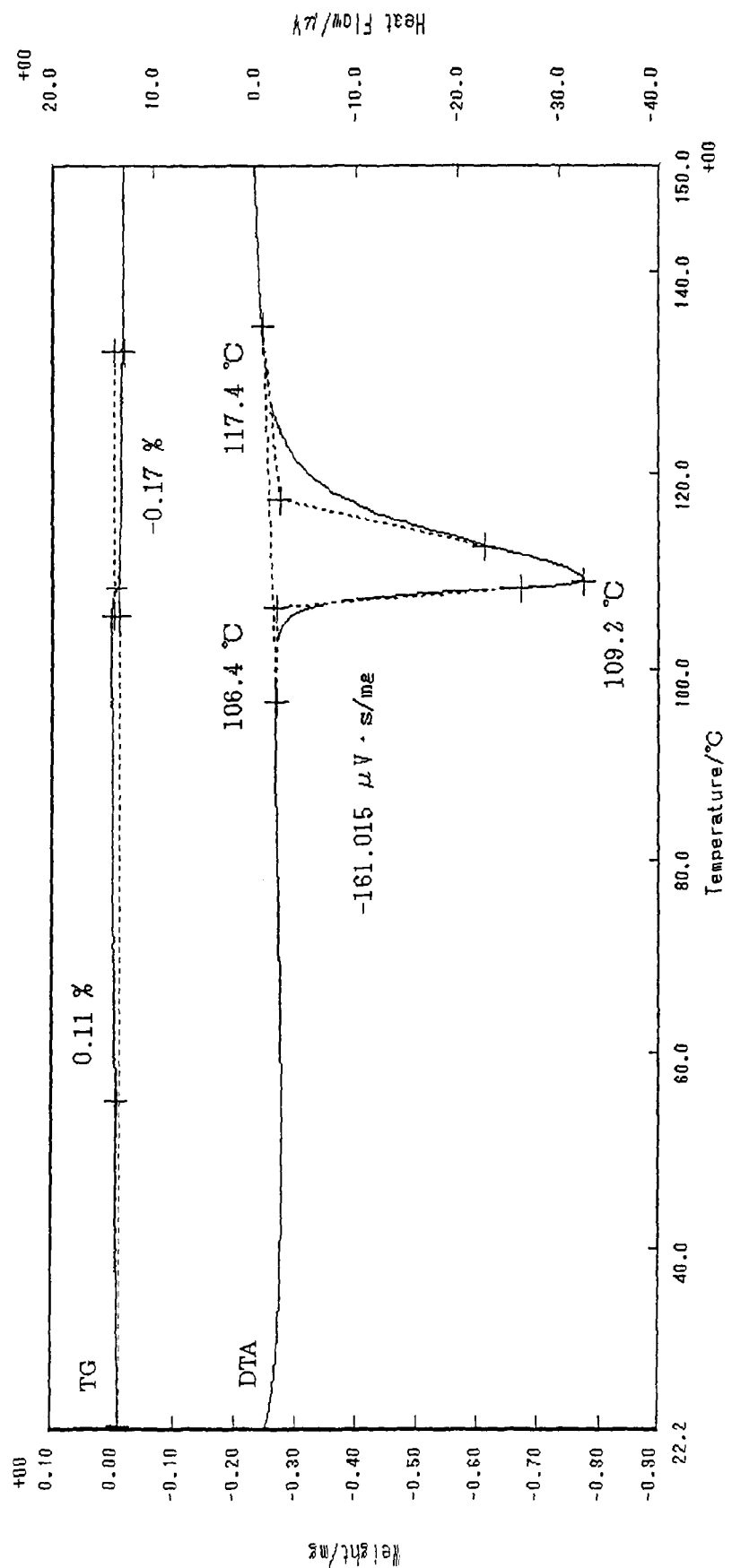
FIG. 19 and FIG. 20 show the results of TG-DTA measurements of 2-[4-[2-(benzothiazol-2-ylthio)ethyl]piperazin-1-yl]-N-[2,6-dimethyl-4-trifluoromethyl-3-pyridyl]acetamide and its dihydrochloride, respectively.
Figure 20:
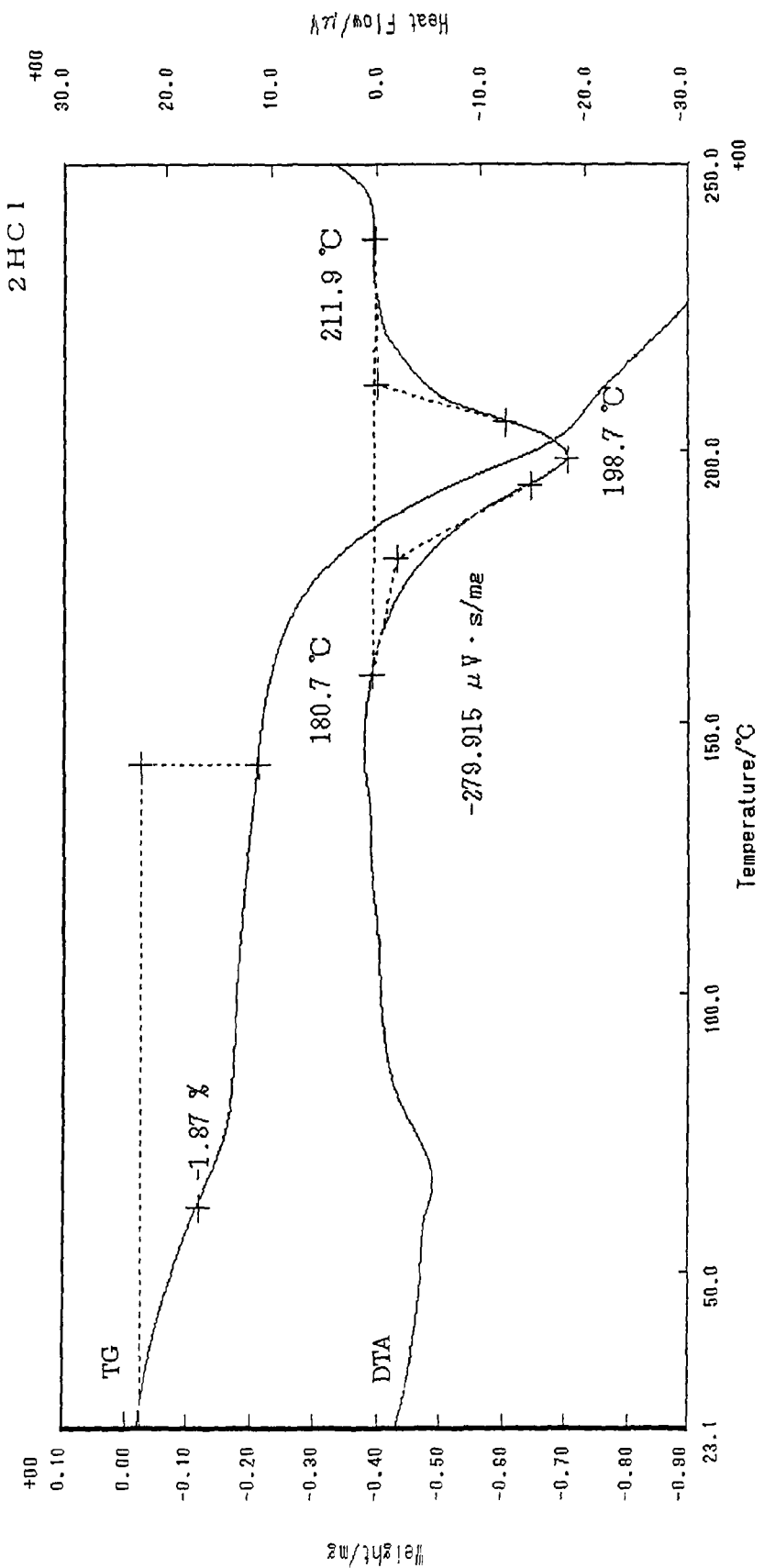

FIG. 19 and FIG. 20 show the results of TG-DTA measurements of 2-[4-[2-(benzothiazol-2-ylthio)ethyl]piperazin-1- yl]-N-[2,6-dimethyl-4-trifluoromethyl-3-pyridyl]acetamide and its dihydrochloride, respectively.

Melting point: 221-212° C.

IR(KBr)cm$^{-1}$: 3427, 1692, 1430, 1389, 1240, 1177, 1154.

$^1$H-NMR (400 MHz, CD$_3$OD) δ: 2.68 (3H, s), 2.81 (3H, s), 3.32-3.45 (4H, m), 3.62-3.73 (6H, m), 3.82 (2H, t, J=6.6 Hz), 4.89 (2H, s), 7.37 (1H, dt, J=1.0, 8.1 Hz), 7.47 (1H, dt, J=1.0, 8.1 Hz), 7.85-7.93 (2H, m), 8.26 (1H, s).

Elemental analysis for C$_{23}$H$_{28}$Cl$_2$F$_3$N$_5$OS$_2$.0.6H$_2$O:

Calculated: C, 46.56; H, 4.96; N, 11.80; Cl, 11.95

Found: C, 46.46; H, 5.07; N, 11.66; Cl, 12.04

Example 6

Preparation of 2-[4-[2-(5-trifluoromethylbenzoxazol-2-ylthio)ethyl]piperazin-1-yl]-N-[2,4-bis(methylthio)-6-methyl-3-pyridyl]acetamide monohydrochloride (1) Preparation of 2-mercapto-5-trifluoromethylbenzoxazole The title compound was obtained by conducting reactions and treatments similar to those described in Example 85 of WO 98/54153 except for the use of 4-trifluoromethylphenol in place of 2-trifluoromethylphenol.

(2) Preparation of 1-[2-(5-trifluoromethylbenzoxazol-2-ylthio)ethyl]piperazine ditrifluoroacetate The title compound was obtained by conducting reactions and treatments similar to those described in Example 22 of WO 98/54153 except for the use of 2-mercapto-5-trifluorobenzoxazole in place of 2-mercaptobenzoxazole.

$^1$H-NMR (400 MHz, DMSO-d$_6$) δ: 2.60-3.20 (10H, m), 3.57 (2H, t, J=6.7 Hz), 7.61 (1H, d, J=8.6 Hz), 7.89 (1H, d, J=8.6 Hz), 8.04 (1H, s), 8.66 (2H, s).

(3) Preparation of 2-[4-[2-(5-trifluoromethylbenzoxazol-2-ylthio)ethyl]piperazin-1-yl]-N-[2,4-bis(methylthio)-6-methyl-3-pyridyl]acetamide The title compound was obtained as a colorless crystalline powder by conducting reactions and treatments similar to those described in Example 24 of WO 98/54153 except for the use of 1-[2-(5-trifluoromethylbenzoxazol-2-ylthio)ethyl] piperazine ditrifluoroacetate in place of 1-[2-(benzoxazol-2-ylthio)ethyl]piperazine ditrifluoroacetate.

Melting point: 103-104° C.

$^1$H-NMR (400 MHz, CDCl$_3$) δ: 2.42 (3H, s), 2.49 (3H, s), 2.52 (3H, s), 2.60-2.82 (8H, m), 2.86 (2H, t, J=6.8 Hz), 3.21 (2H, s), 3.51 (2H, t, J=6.8 Hz), 6.67 (1H, s), 7.51-7.53 (2H, m), 7.85 (1H, s), 8.55 (1H, s).

(4) Preparation of 2-[4-[2-(5-trifluoromethylbenzoxazol-2-ylthio)ethyl]piperazin-1-yl]-N-[2,4-bis(methylthio)-6-methyl-3-pyridyl]acetamide monohydrochloride 2-[4-[2-(5-Trifluoromethylbenzoxazol-2-ylthio)ethyl] piperazin-1-yl]-N-[2,4-bis(methylthio)-6-methyl-3-pyridyl] acetamide (200 mg, 0.35 mmol) was dissolved in ethanol (4 mL), followed by the addition of pyridine hydrochloride (82 mg, 0.70 mmol). The reaction mixture was concentrated, and to the residue, ethanol (0.5 mL) and water (5 mL) were added. A precipitate was collected by filtration to obtain the title compound (180 mg, 85%) as a colorless crystalline powder.

Figure 21:
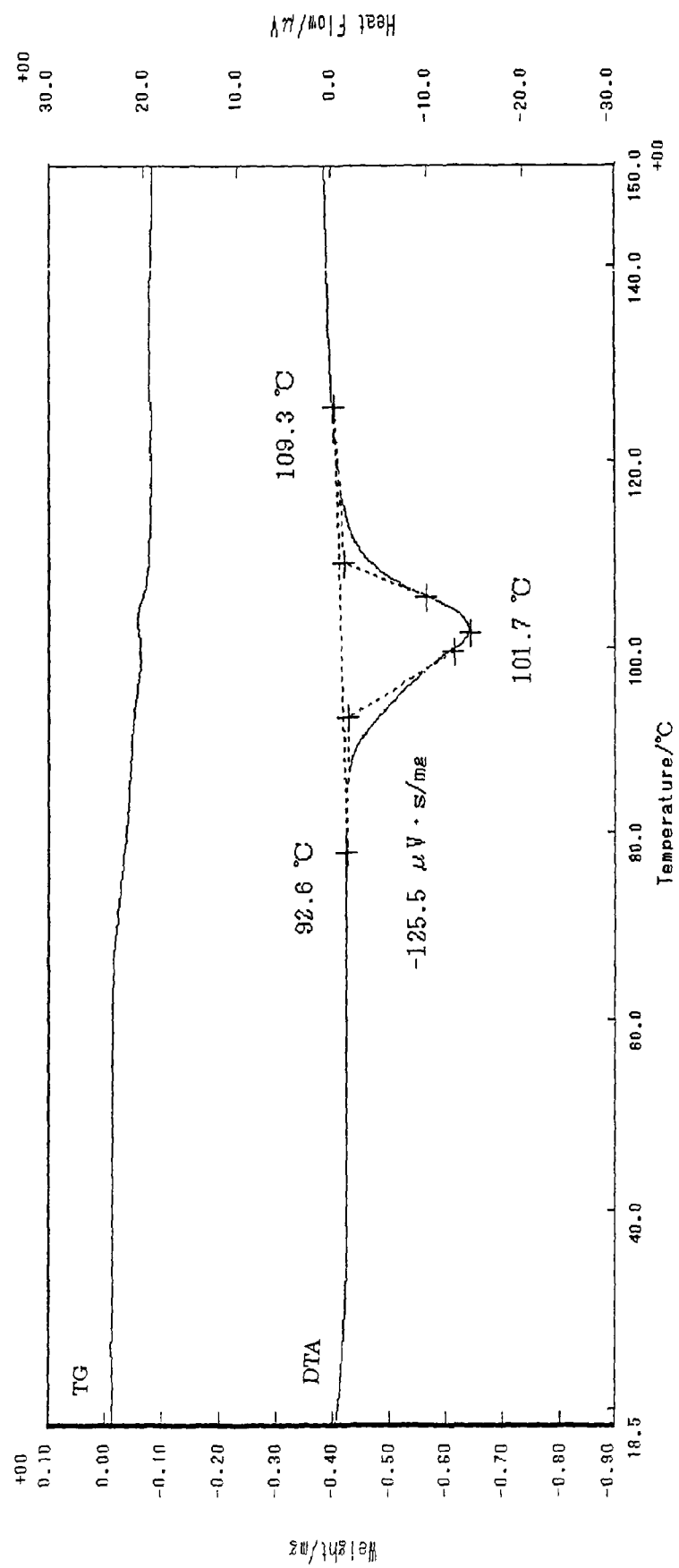
FIG. 21 and FIG. 22 show the results of TG-DTA measurements of 2-[4-[2-(5-trifluoromethylbenzoxazol-2-ylthio)ethyl]piperazin-1-yl]-N-[2,4-bis(methylthio)-6-methyl-3-pyridyl]acetamide and its monohydrochloride, respectively.
Figure 22:
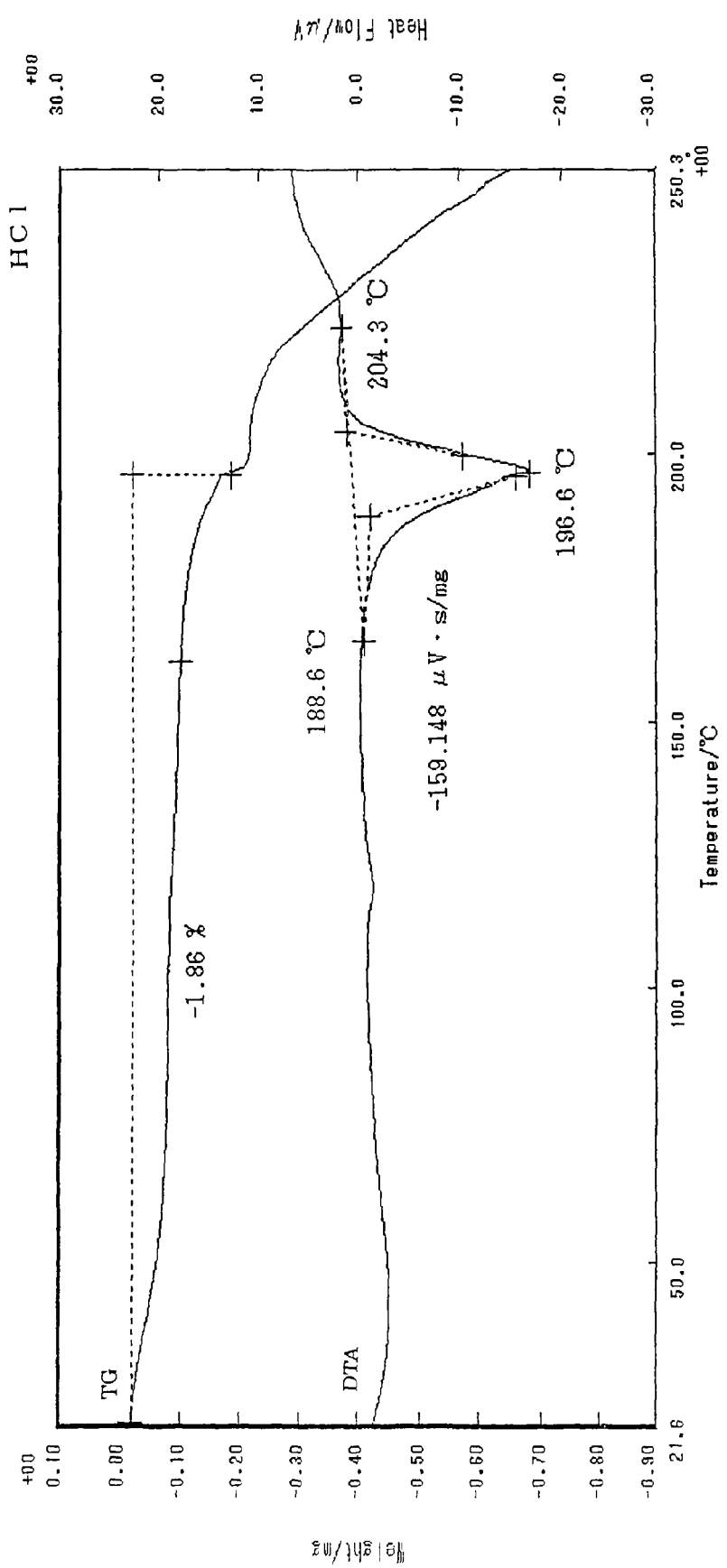

FIG. 21 and FIG. 22 show the results of TG-DTA measurements of 2-[4-[2-(5-trifluoromethylbenzoxazol-2-ylthio) ethyl]piperazin-1-yl]-N-[2,4-bis(methylthio)-6-methyl-3-pyridyl]acetamide and its monohydrochloride, respectively.

Melting point: 195-196° C.

IR(KBr)cm$^{-1}$: 3427, 1685, 1501, 1437, 1327, 1143, 1123.

$^1$H-NMR (400 MHz, DMSO-d$_6$) δ: 2.42 (3H, s), 2.43 (3H, s), 2.46 (3H, s), 2.70-3.84 (14H, m), 6.94 (1H, s), 7.72 (1H, d, J=8.3 Hz), 7.91 (1H, d, J=8.3 Hz), 8.06 (1H, s).

Elemental analysis for C$_{24}$H$_{29}$ClF$_3$N$_5$O$_2$S$_3$.0.5H$_2$O:

Calculated: C, 46.71; H, 4.90; N, 11.35

Found: C, 46.67; H, 4.89; N, 11.33

Example 7

Preparation of 2-[4-[2-(benzoxazol-2-ylthio)ethyl] piperazin-1-yl]-N-[2-(2-methoxyethoxy)-4-(2,2,2-trifluoroethoxy)-6-methyl-3-pyridyl]acetamide monohydrochloride (1) Preparation of 2-[4-[2-(benzoxazol-2-ylthio) ethyl]piperazin-1-yl]-N-[2-(2-methoxyethoxy)-4-(2, 2,2-trifluoroethoxy)-6-methyl-3-pyridyl]acetamide The title compound was obtained by conducting a reaction and treatments similar to those described in the procedure (1) of Example 3 except that 2-bromo-N-[2-(2-methoxyethoxy)-6-methyl-4-(2,2,2-trifluoroethoxy)-3-pyridyl]acetamide was used in place of 2-bromo-N-[2,4-bis(2,2,2-trifluoroethoxy)-6-methyl-3-pyridyl]acetamide and 1-[2-(benzoxazol-2-ylthio)ethyl]piperazine dihydrochloride was used in lieu of 1-[2-(benzimidazol-2-ylthio)ethyl]piperazine trihydrochloride.

(2) Preparation of 2-[4-[2-(benzoxazol-2-ylthio) ethyl]piperazin-1-yl]-N-[2-(2-methoxyethoxy)-4-(2, 2,2-trifluoroethoxy)-6-methyl-3-pyridyl]acetamide monohydrochloride 2-[4-[2-(Benzoxazol-2-ylthio)ethyl]piperazin-1-yl]-N-[2-(2-methoxyethoxy)-4-(2,2,2-trifluoroethoxy)-6-methyl-3-pyridyl]acetamide (500 mg, 0.86 mmol) was dissolved in ethanol (10 mL), followed by the addition of pyridine hydrochloride (198 mg, 1.71 mmol). The reaction mixture was concentrated, and to the residue, ethanol (0.2 mL) and water (2 mL) were added. A precipitate was collected by filtration to afford the title compound (134 mg, 25.2%) as a colorless crystalline powder.

Figure 23:
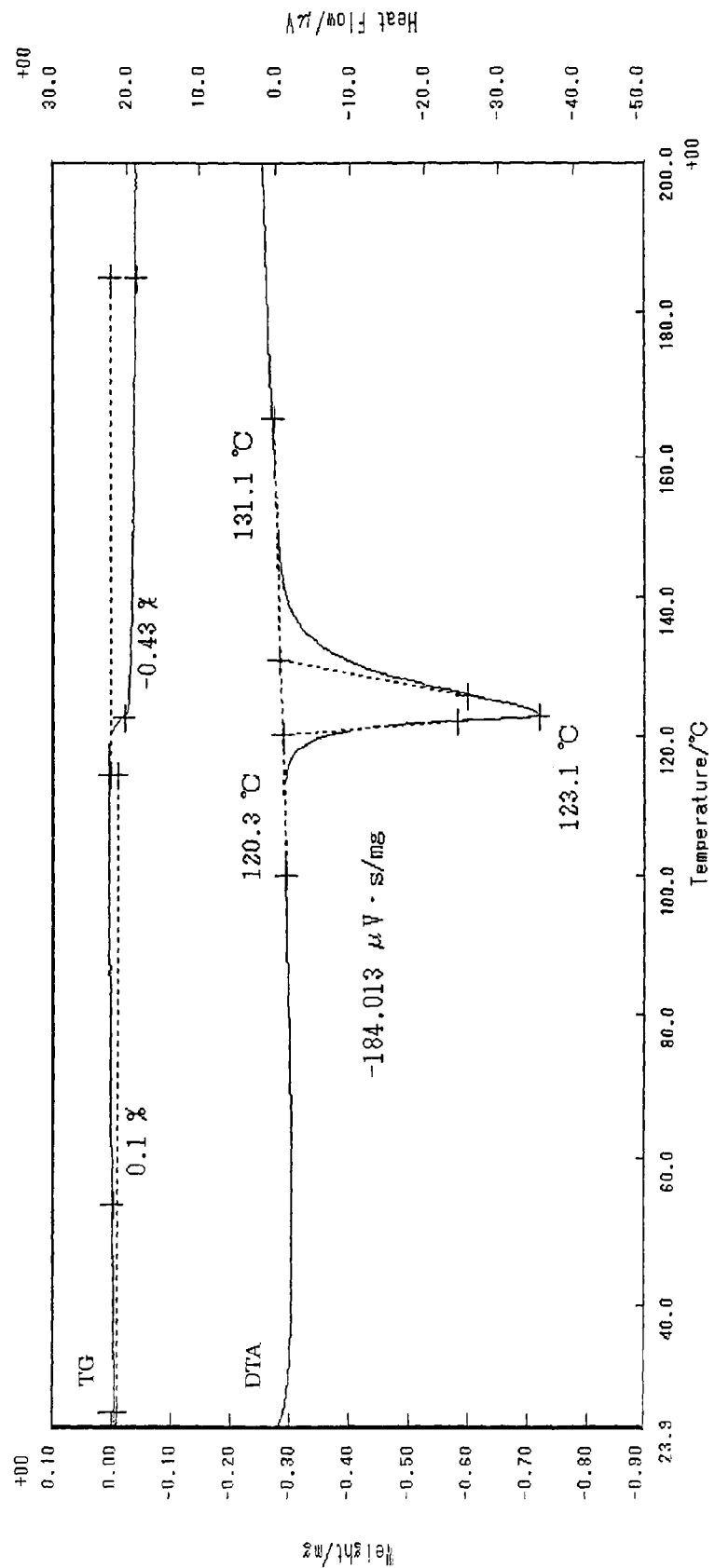
FIG. 23 and FIG. 24 show the results of TG-DTA measurements of 2-[4-[2-(benzoxazol-2-ylthio)ethyl]piperazin-1-yl]-N-[2-(2-methoxyethoxy)-4-(2,2,2-trifluoroethoxy)-6-methyl-3-pyridyl]acetamide and its monohydrochloride, respectively.
Figure 24:
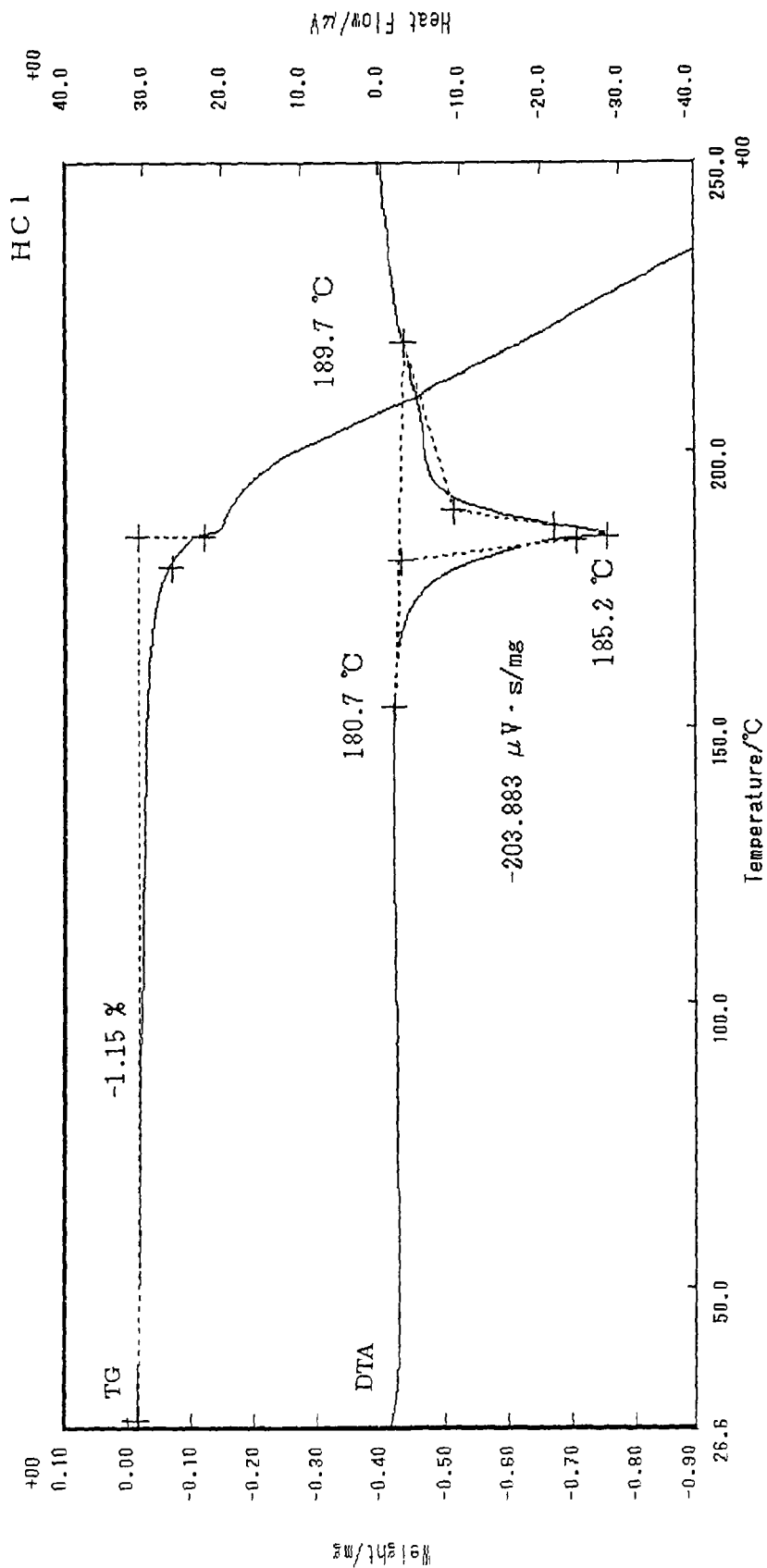

FIG. 23 and FIG. 24 show the results of TG-DTA measurements of 2-[4-[2-(benzoxazol-2-ylthio)ethyl]piperazin-1-yl]-N-[2-(2-methoxyethoxy)-4-(2,2,2-trifluoroethoxy)-6-methyl-3-pyridyl]acetamide and its monohydrochloride, respectively.

Melting point: 181-182° C.

IR(KBr)cm$^{-1}$: 3432, 1686, 1593, 1507, 1454, 1170, 1137.

$^1$H-NMR (400 MHz, CD$_3$CN) δ: 2.38 (3H, s), 2.92-3.26 (8H, m), 3.31 (3H, s), 3.42-3.59 (4H, m), 3.62 (2H, t, J=4.9 Hz), 3.72-3.84 (2H, m), 4.38 (2H, t, J=4.9 Hz), 4.54 (2H, q, J=8.3 Hz), 6.61 (1H, s), 7.28-7.36 (2H, m), 7.54 (2H, dd, J=2.2, 5.6 Hz), 8.19 (1H, br).

Elemental analysis for C$_{26}$H$_{33}$ClF$_3$N$_5$O$_5$S.0.4H$_2$O

Calculated: C, 49.78; H, 5.43; N, 11.16; Cl, 5.65

Found: C, 49.76; H, 5.31; N, 11.25; Cl, 5.78

The invention claimed is:

1. A method for preparing a monohydrochloride of a piperazine derivative represented by the following formula (1) or a water adduct of said monohydrochloride acid addition salt, comprising:
reacting the piperazine derivative with a hydrochloric acid salt of pyridine thus forming a monohydrochloride acid addition salt of said piperazine derivative,
wherein said piperazine derivative is characterized by formula (1):

(1)

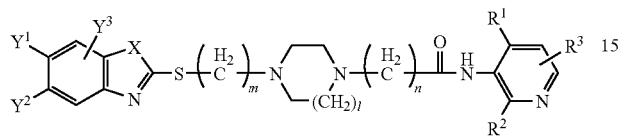

wherein
X represents an oxygen atom,
$Y^1$, $Y^2$ and $Y^3$ each independently represent a hydrogen or halogen atom or a lower alkyl or lower haloalkyl group,
$R^1$, $R^2$ and $R^3$ each independently represents a hydrogen or halogen atom or a lower alkyl, lower haloalkyl, lower alkylthio, lower haloalkoxy or lower alkoxyalkoxy group,
l denotes an integer of from 1 to 2,
m denotes an integer of from 2 to 4, and
n denotes an integer of from 1 to 3.

2. The method of claim 1, wherein said piperazine derivative is represented by the following formula (2):

(2)

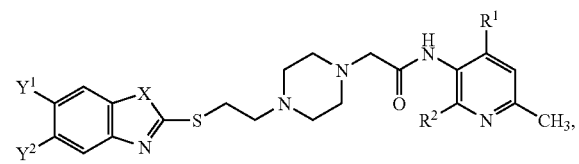

wherein
X represents an oxygen atom,
$Y^1$ and $Y^2$ each independently represents a hydrogen or halogen atom or a trifluoromethyl group, and
$R^1$ and $R^2$ each independently represent a methyl, trifluoromethyl, methylthio, trifluoroethoxy or methoxyethoxy group.

3. The method of claim 1, wherein the piperazine derivative is:
2-[4-[2-(benzoxazol-2-ylthio)ethyl]piperazin-1-yl]-N-[2,4-bis(2,2,2-trifluoroethoxy)-6-methyl-3-pyridyl]acetamide,
2-[4-[2-(5-trifluoromethylbenzoxazol-2-ylthio)ethyl]piperazin-1-yl]-N-[2,4-bis(methylthio)-6-methyl-3-pyridyl]acetamide, or
2-[4-[2-(benzoxazol-2-ylthio)ethyl]piperazin-1-yl]-N-[2-(2-methoxyethoxy)-4-(2,2,2-trifluoroethoxy)-6-methyl-3-pyridyl]acetamide.

4. The method of claim 1, wherein said acid salt of pyridine is prepared from 1.0 to 1.5 equivalents of pyridine to 1 equivalent of hydrochloric acid.

5. The method of claim 1, further comprising precipitating crystals of said monohydrochloride acid addition salt and recovering the crystals; and, optionally, washing and/or drying the recovered crystals.

6. The method of claim 1, wherein said reacting occurs in an anhydrous organic solvent.

7. The method of claim 1, wherein said reacting occurs in an organic solvent containing water.

8. The method of claim 1, wherein said reacting occurs in an organic solvent selected from the group consisting of methanol, ethanol, isopropanol, dioxane, tetrahydrofuran, acetone and acetonitrile.

9. The method of claim 1, wherein said monohydrochloride acid addition salt of a piperazine derivative or said water adduct of said monohydrochloride is prepared from 1.0 to 3.0 equivalents of pyridine hydrochloride.

10. A monohydrochloride of a piperazine derivative represented by formula (2):

(2)

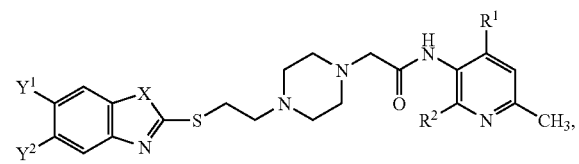

wherein
X represents —NH—, —S—, or —O—,
$Y^1$ and $Y^2$ each independently represent a hydrogen, a halogen atom or a trifluoromethyl group, and
$R^1$ and $R^2$ each independently represent a methyl, trifluoromethyl, methylthio, trifluoroethoxy or methoxyethoxy group;
or a water adduct thereof.

11. The monohydrochloride of the compound of claim 10, wherein X represents —NH— or a water adduct thereof.

12. The monohydrochloride of claim 10, which is selected from the group consisting of:
2-[4-[2-(benzimidazol-2-ylthio)ethyl]piperazin-1-yl]-N-[2,4-bis(methylthio)-6-methyl-3-pyridyl]acetamide monohydrochloride or a water adduct thereof, and
2-[4-[2-(5,6-difluorobenzimidazol-2-ylthio)ethyl]piperazin-1-yl]-N-[2,4-bis(2,2,2-trifluoroethoxy)-6-methyl-3-pyridyl]acetamide monohydrochloride; or a water adduct thereof.

13. The monohydrochloride of claim 12 that is a crystal; or a water adduct thereof.

14. The monohydrochloride of claim 10 that is a 0.9 water adduct of 2-[4-[2-(benzimidazol-2-ylthio)ethyl]piperazin-1-yl]-N-[2,4-bis(methylthio)-6-methyl-3-pyridyl]acetamide monohydrochloride.

15. A pharmaceutical composition comprising the monohydrochloride of claim 10; or a water adduct thereof.

16. The monohydrochloride of claim 10, wherein X is —O—; or a water adduct thereof.

17. The monohydrochloride of claim 16 that is 2-[4-[2-(benzoxazol-2-ylthio)ethyl]piperazin-1-yl]-N-[2,4-bis(2,2,2-trifluoroethoxy)-6-methyl-3-pyridyl]acetamide monohydrochloride,
2-[4-[2-(5-trifluoromethylbenzoxazol-2-ylthio)ethyl]piperazin-1-yl]-N-[2,4-bis(methylthio)-6-methyl-3-pyridyl]acetamide monohydrochloride, or
2-[4-[2-(benzoxazol-2-ylthio)ethyl]piperazin-1-yl]-N-[2-(2-methoxyethoxy)-4-(2,2,2-trifluoroethoxy)-6-methyl-3-pyridyl]acetamide monohydrochloride; or
a water adduct thereof.

18. The monohydrochloride of claim 17 that is a crystal; or a water adduct thereof.

19. The monohydrochloride or water adduct of claim 10, wherein at least one of $Y^1$ and $Y^2$ is hydrogen.

20. The monohydrochloride or water adduct of claim 10, wherein at least one of $Y^1$ and $Y^2$ is a halogen atom.

21. The monohydrochloride or water adduct of claim 10, wherein at least one of $Y^1$ and $Y^2$ is a trifluoromethyl group.

22. The monohydrochloride or water adduct of claim 10, wherein at least one of $R^1$ and $R^2$ is methyl, trifluoromethyl, methylthio, trifluoroethoxy or methoxyethoxy group.

23. The monohydrochloride or water adduct of claim 10, wherein at least one of $R^1$ and $R^2$ is trifluoromethyl.

24. The monohydrochloride or water adduct of claim 10, wherein at least one of $R^1$ and $R^2$ is methylthio.

25. The monohydrochloride or water adduct thereof of claim 10, wherein at least one of $R^1$ and $R^2$ is trifluoroethoxy.

26. The monohydrochloride or water adduct thereof of claim 10, wherein at least one of $R^1$ and $R^2$ is methoxyethoxy.

27. The monohydrochloride or water adduct thereof of claim 10 that is made by reacting a piperazine derivative with a hydrochloric acid salt of pyridine.

28. The monohydrochloride or water adduct thereof of claim 10 that has no hygroscopicity or that has a lower hygroscopicity than a corresponding dihydrochloride of formula (II).

29. The monohydrochloride or water adduct thereof of claim 10 that has a higher degree of crystallinity than a corresponding dihydrochloride of formula (II).

30. The monohydrochloride or water adduct thereof of claim 10 that is free from the residual influence of hydrochloric acid.

\* \* \* \* \*